(12) United States Patent
Klassen et al.

(10) Patent No.: US 11,413,580 B2
(45) Date of Patent: Aug. 16, 2022

(54) BIOLOGICAL FLUID PURIFICATION WITH BIOCOMPATIBLE MEMBRANES

(71) Applicant: IVIVA Medical, Inc., Woburn, MA (US)

(72) Inventors: Charles C. Klassen, Boston, MA (US); Harald C. Ott, Wenham, MA (US); Maria Jaramillo, Swampscott, MA (US); Robert G. Hesse, Watertown, MA (US); Daniel Cheng, Somerville, MA (US)

(73) Assignee: IVIVA Medical, Inc., Woburn, MA (US)

( * ) Notice: Subject to any disclaimer, the term of this patent is extended or adjusted under 35 U.S.C. 154(b) by 0 days.

(21) Appl. No.: 17/435,024

(22) PCT Filed: Feb. 28, 2020

(86) PCT No.: PCT/US2020/020498
§ 371 (c)(1),
(2) Date: Aug. 30, 2021

(87) PCT Pub. No.: WO2020/176888
PCT Pub. Date: Sep. 3, 2020

(65) Prior Publication Data
US 2022/0133973 A1    May 5, 2022

Related U.S. Application Data

(60) Provisional application No. 62/812,239, filed on Feb. 28, 2019.

(51) Int. Cl.
*B01D 61/18* (2006.01)
*A61M 1/16* (2006.01)
(Continued)

(52) U.S. Cl.
CPC .............. *B01D 61/18* (2013.01); *A61L 27/40* (2013.01); *A61M 1/16* (2013.01); *A61M 1/1678* (2013.01); *A61M 1/1696* (2013.01); *A61M 1/28* (2013.01); *A61M 1/3417* (2014.02); *A61M 1/3489* (2014.02); *B01D 61/14* (2013.01);
(Continued)

(58) Field of Classification Search
CPC ....... A61L 27/40; A61M 1/16; A61M 1/1678; A61M 1/1696; A61M 1/28; A61M 1/3417; A61M 1/3489; A61M 2202/0021; A61M 2202/0413; A61M 2205/02;
(Continued)

(56) References Cited

U.S. PATENT DOCUMENTS

| 4,857,199 A | 8/1989 | Cortial |
| 2004/0147042 A1 | 7/2004 | Gratzl et al. |
| 2012/0184940 A1 | 7/2012 | Ying |

FOREIGN PATENT DOCUMENTS

GB    2 010 121 A    6/1979

OTHER PUBLICATIONS

International Search Report Issued in Application No. PCT/US2020/020498, dated May 7, 2020.

*Primary Examiner* — John Kim
(74) *Attorney, Agent, or Firm* — Morse, Barnes-Brown & Pendleton, P.C.; Lisa M. Warren, Esq.

(57) ABSTRACT

Disclosed are apparatus and methods for blood and other biological fluid purification using a membrane with cell containing vascular channel systems and filtration channel systems. Also disclosed are methods of making the apparatus as well as methods of making membranes.

20 Claims, 13 Drawing Sheets

(51) Int. Cl.
- *A61M 1/34* (2006.01)
- *B01D 63/06* (2006.01)
- *B01D 61/14* (2006.01)
- *A61M 1/28* (2006.01)
- *A61L 27/40* (2006.01)
- *B01D 61/28* (2006.01)

(52) U.S. Cl.
CPC .............. *B01D 61/28* (2013.01); *B01D 63/06* (2013.01); *A61M 2202/0021* (2013.01); *A61M 2202/0413* (2013.01); *A61M 2205/02* (2013.01); *A61M 2205/75* (2013.01)

(58) Field of Classification Search
CPC ... A61M 2205/75; B01D 61/14; B01D 61/18; B01D 61/28; B01D 63/06
See application file for complete search history.

BIOLOGICAL FLUID PURIFICATION WITH BIOCOMPATIBLE MEMBRANES

CROSS-REFERENCE TO RELATED APPLICATIONS

This application is a national stage filing under 35 U.S.C. 371 of International Application No.: PCT/US2020/020498, filed Feb. 28, 2020, which claims the benefit of U.S. Provisional Application 62/812,239, filed on Feb. 28, 2019. The entire teachings of the above applications are incorporated herein by reference. International Application No.: PCT/US2020/020498 was published under PCT Article 21(2) in English.

BACKGROUND OF THE INVENTION

Current methods of artificial blood purification require the use of dialysate filters (in conventional hemodialysis), the use of a dialysis fluid (in both conventional dialysis and peritoneal dialysis), the use of replacement fluid (in hemofiltration and hemodiafiltration), the use of anticoagulation to prevent activation of the clotting cascade by the filter material (conventional hemodialysis), the use of blood pumps to generate the necessary flow and hydrostatic gradient to enable filtration and dialysis (conventional hemodialysis), and, in some applications, the use of adsorbent materials to bind toxin molecules.

Currently, no technology exists to create a blood purification system that can function continuously without the need for these components, in a fully integrated, possibly implantable device. Further, bioengineering of tissues and organ grafts of human scale, which could address the issues discussed above, requires the generation of a matrix that provides the necessary functional architecture to allow each cell to fulfill their specific roll and generate functional tissue constructs. Tissues and organs that contain one or more epithelial structures (digestive, endocrine, nervous, lymphatic, integumentary, reproductive, respiratory, sensory, urinary, and circulatory) depend on the presence of a thin basement membrane that enables functions such as filtration of fluid (kidney, eye, lymphatic, brain), diffusion of gases (lung), secretion and absorption of electrolytes and other molecules (kidney, gut, liver, enteric tissue), and diffusion of hormones (pancreas, pituitary gland, adrenal gland) from one lumen or compartment to another. In many instances, this basement membrane has to be <1 um or <10 um thick to enable function (See, Rayat et al., *Indian journal of pathology & microbiology* 48, 453-458 (2005) and Kopf et al., *Nature immunology* 16, 36-44 (2015)).

Currently, no technology exists to generate a membrane composed of biologic and/or native matrix materials with the requisite tunable micro or nano porosity and physiologic thickness to enable such function in a biologic tissue scaffold, such as for an artificial tissue or organ for hemodialysis.

SUMMARY OF THE INVENTION

Work described herein demonstrates manufacture of biocompatible membranes with tunable thickness and pore size.

Furthermore, the work herein demonstrates the design, manufacturing, and use of an integrated adaptive biologic blood purification (IABBP) device having biocompatible membranes. The purpose of the device is to remove toxins and excess water from the patient's circulation to replace the human body's own purification systems such as the kidney and the liver. In contrast to currently available systems, the device's function does not depend on the use of an extrinsic dialysate fluid (such as is used in hemodialysis and peritoneal dialysis), replacement fluid (such as is used in hemofiltration and hemodiafiltration) or adsorbent material (such as is used in portable dialysis and extracorporeal liver replacement). The IABBP device is connected to a patient's vascular system via a direct connection to an artery and a vein. The patient's cardiovascular system is used to perfuse the IABBP device with sufficient blood flow to enable its function. This can be achieved without the use of additional mechanical pumps. However, in some instances, pumps may be used to increase IABBP device function.

The connection to the patient's vascular system is established via cannulation of an arteriovenous shunt or a large vein, or via direct anastomosis of the IABBP devices vascular conduits to the patient's vasculature. The IABBP device can be used in an extracorporeal fashion or can be implanted into the patient similar to a donor organ. The IABBP device can be used in continuous fashion or for intermittent treatments. The IABBP device produces a filtrate that is drained into an extracorporeal collection system or connected to the patient's bladder via surgical anastomosis.

The IABBP can be manufactured by creating a scaffold that is subsequently repopulated with cells and cultured to mature the resulting tissue to function. The IABBP scaffold is generated by combining multiple functional units. Each functional unit is generated by producing a biocompatible extracellular matrix membrane. This membrane can be porous or non-porous depending on the functional requirements. A sacrificial material is then printed onto the membrane on both sides. The entire membrane is then embedded into a matrix material. The sacrificial material is removed, which results in two channel systems separated by the membrane. Several functional units can be stacked to generate a scaffold of sufficient size to meet the requirements of the human body. Both channel systems can then be repopulated with cells to generate functional, live tissue.

Some aspects of the disclosure are related to an apparatus for integrated adaptive biologic blood purification comprising a functional unit comprising a membrane comprising a vascular surface and a filtration surface; a vascular channel system comprising a first luminal space, adhered to and in fluid communication with the vascular surface of the membrane, and comprising a first end configured to connect in fluid communication to a fluid supply and a second end configured to connect in fluid communication to a filtered fluid outlet; a filtration channel system comprising a second luminal space, adhered to and in fluid communication with the filtration surface of the membrane, and comprising a third end configured to connect in fluid communication to a filtrate outlet; wherein the vascular channel system and the filtration channel system are in fluid communication with each other across the membrane; wherein the functional unit further comprises at least three segments, including at least a filtration segment configured to provide ultrafiltration producing a primary ultrafiltrate, connecting to a tubular segment configured to provide reabsorption producing a secondary ultrafiltrate, connecting to a ductal segment configured to provide concentration producing a tertiary ultrafiltrate; and wherein the membrane comprises three membrane segments including at least a filtration membrane segment, a tubular membrane segment and a ductal membrane segment.

In some embodiments, the membrane comprises a biocompatible extracellular matrix membrane separating the vascular channel system from the filtration channel system, and the biocompatible extracellular matrix membrane is embedded into a matrix material. In some embodiments, the biocompatible extracellular matrix membrane comprises a collagen membrane with a thickness of 0.1-10 micrometers (0.1-10 μm) that supports cell adhesion on both the vascular surface and the filtration surface of the collagen membrane. In some embodiments, the matrix material is gelatin. In some embodiments, the biocompatible extracellular matrix membrane comprises fibers, nano-fibers, or other longitudinal elements. In some embodiments, the fibers, nano-fibers, or other longitudinal elements increase or modulate the mechanical strength of the membrane. In some embodiments, the fibers, nano-fibers, or other longitudinal elements are evenly distributed throughout the membrane and provide homogenous mechanical strengthening. In some embodiments, the fibers, nano-fibers, or other longitudinal elements are heterogeneously distributed in the membrane and provide heterogeneous mechanical strengthening.

In some embodiments, the filtration membrane segment enables production of a filtrate from the first luminal space in the vascular channel system to the second luminal space of the filtration channel system; the tubular membrane segment enables solute and water exchange and/or diffusion between the vascular channel system and the filtration channel system; and the ductal membrane segment enables transfer of water and solutes from the filtration channel system to the vascular channel system.

In some embodiments, the functional unit comprises at least one biological fluid inflow conduit in fluid communication with the first end of the vascular channel system and the first luminal space and at least one biological fluid outflow conduit in fluid communication with the second end of the vascular channel system and the first luminal space, wherein the functional unit comprises at least one filtrate outflow conduit in fluid communication with the third end of the filtration channel system and the second luminal space, and wherein the functional unit further comprises one or more vascular segment conduits interconnecting the filtration segment, the tubular segment and the ductal segment of the vascular channel system and the first luminal space and one or more filtration segment conduits interconnecting the filtration segment, the tubular segment and the ductal segment of the filtration channel system and the second luminal space.

In some embodiments, the at least one biological fluid inflow conduit is in fluid communication with an arterial conduit, the at least one biological fluid outflow conduit is in fluid communication with a vascular conduit, and the at least one filtrate outflow conduit is in fluid communication with a drain conduit. In some embodiments, the apparatus produces an ultrafiltrate that is drained, using a drain conduit, into an extracorporeal collection system or drained, using a drain conduit, into a patient bladder. In some embodiments, the first luminal space and the second luminal spaces are embedded in a scaffold.

In some embodiments, the filtration segment of the vascular channel system comprises vascular channel walls lined with endothelial cells selected from primary human glomerular endothelial cells, induced pluripotent stem cell (iPSC) derived endothelial cells, and/or human umbilical cord endothelial cells. In some embodiments, the tubular segment of the vascular channel system comprises vascular channel walls lined with endothelial cells selected from primary human peritubular capillary endothelial cells, iPSC derived endothelial cells, and/or human umbilical cord endothelial cells. In some embodiments, the ductal segment of the vascular channel system comprises vascular channel walls lined with endothelial cells selected from primary human renal medullary endothelial cells, iPSC derived endothelial cells, and/or human umbilical cord endothelial cells. In some embodiments, the filtration segment of the filtration channel system comprises filtration channel walls lined with epithelial cells selected from primary human podocytes and/or human iPSC derived podocytes. In some embodiments, the tubular segment of the filtration channel system comprises filtration channel walls lined with epithelial cells selected from primary human tubular epithelial cells and/or iPSC derived tubular epithelial cells.

In some embodiments, the ductal segment of the filtration channel system comprises filtration channel walls lined with epithelial cells selected from primary human tubular epithelial cells and/or iPSC derived tubular epithelial cells.

In some embodiments, the apparatus comprises a plurality of functional units, including the functional unit and additional functional units of a same configuration, wherein each functional unit of the plurality of functional units has a first end of a vascular channel system and first luminal space in fluid communication with the at least one biological fluid inflow conduit; a second end of a vascular channel system and first luminal space in fluid communication with the at least one biological fluid outflow conduit, and a third end of a filtration channel system and second luminal space in fluid communication with a filtrate outflow conduit; wherein each first end of the plurality of functional units connects individually and in parallel to one of a plurality of manifold ports of the at least one biological fluid inflow conduit; wherein each second end of the plurality of functional units connects individually and in parallel to one of a plurality of manifold ports of the at least one biological fluid outflow conduit; and wherein each third end of the plurality of functional units connects individually and in parallel to one of a plurality of manifold ports of the at least one filtrate outflow conduit. In some embodiments, the apparatus comprises the plurality of functional units, including the functional unit and the additional functional units of a same configuration, stacked in parallel layers of functional units.

In some embodiments, the at least one biological fluid inflow conduit comprises a blood inlet conduit configured to transport a Blood inflow, the at least one biological fluid outflow conduit comprises a blood outflow conduit configured to transport a blood outflow, and parallel layers of functional units configured for biologic blood purification.

In some embodiments, the filtration segment of the filtration channel system is configured to provide ultrafiltration producing a primary ultrafiltrate, the tubular segment is configured to provide reabsorption producing a secondary ultrafiltrate flow by solute and water absorption, and the ductal segment is configured to provide concentration producing a tertiary ultrafiltrate flow by water absorption.

In some embodiments, the apparatus is configured for extracorporeal operation in a sterile, heated enclosure. In some embodiments, the apparatus is disposed within a capsule, and sized and configured for placement within a human body to replace or augment a kidney or liver function. In some embodiments, the membrane comprises a porous membrane that comprises pores disposed to interconnect the vascular surface and the filtration surface. In some embodiments, the pores have a diameter of pores have a diameter of between 1 μm and 15 μm.

Some aspects of the disclosure are related to a method of treating a patient having an insufficient kidney or liver function comprising fluidly connecting the apparatus described herein to the circulation system of the patient and passing patient blood through the vascular channel system of the apparatus from the filtration member segment to the tubular member segment, from the tubular member segment to the ductal member segment, and from the ductal member segment back into the circulation system of the patient. In some embodiments, the apparatus is implanted in the patient. In some embodiments, ultrafiltrate produced by the apparatus is delivered extracorporeal to the patient. In some embodiments, the ultrafiltrate produced by the apparatus is delivered to the bladder of the patient.

In some embodiments, the apparatus is extracorporeal to the patient.

Some aspects of the disclosure are related to a method of manufacturing the apparatus described herein, comprising providing a plurality of membranes having a sacrificial material in the form of the vascular channel network on the vascular surface and having sacrificial material in the form of the filtration channel system on the filtration surface, submerging the plurality of membranes in a solution (i.e., membrane solution) comprising a scaffold material, gelating the scaffold material, and removing the sacrificial material to thereby form the luminal spaces of the vascular channel system and the filtration channel system.

In some embodiments, the plurality of membranes are each generated by chemical or physical thin film deposition, atomization, spraying, electrospinning, dip coating, or gelation of a solution comprising decellularized tissue, gelatin, gelatin composites, collagen, fibrin, hydrogel, hydrogel composites, chitosan, nitrocellulose, polylactic acid, or extra-cellular matrix that has been liquefied or homogenized, in a thin film layer followed by curing, crosslinking, polymerizing, drying, or gelating the solution to form a membrane layer.

In some embodiments, the membrane solution further comprises a porogen homogenously mixed therein. In some embodiments, the porogen is a self-assembling tri-block copolymer. In some embodiments, the self-assembling tri-block copolymer is a poloxamer formulation, preferably Pluronic F127 at a concentration of 1-40% wt.

In some embodiments, the membrane solution further comprises one or more agents modifying the mechanical or biological properties of the one or more membranes. In some embodiments, the one or more agents are selected from glycerin, sorbitol, propylene glycol, plasticizers, fibers or other longitudinal elements, and encapsulated growth factors. In some embodiments, the membrane solution further comprises fibers, nanotubes, or other longitudinally oriented materials in order to provide improved mechanical properties. These fibers can be mixed into the membrane solution prior to fabrication in order evenly distribute the fibers throughout the membrane. Alternatively, these fibers can be deposited or integrated onto the membrane after fabrication through techniques such as electrospinning, 3D printing, or other techniques. The fibers may be homogenously distributed throughout the membrane or may be distributed in an organized manner to provide heterogenous mechanical properties for the membrane. In some embodiments, the method of generating a thin film layer is repeated one or more times to generate a membrane or membranes having two or more membrane layers. In some embodiments, the two or more layers are generated from solutions having different components, agents and/or concentrations.

In some embodiments, at least one of the plurality of membranes are treated to remove the porogen, thereby forming pores in the membrane.

In some embodiments, the membrane solution comprises 3-35 wt % of gelatin or a gelatin-polymer composite. In some embodiments, the thin film layer is crosslinked with a solution comprising glutaraldehyde, transglutaminase, or other crosslinking enzymes or molecules.

In some embodiments, the sacrificial material has a thermally reversible gelation property or can be dissolved in non-polar solvent. In some embodiments, the sacrificial material is removed with a non-polar solvent or by thermally reversing gelation. In some embodiments, the sacrificial material comprises a poloxamer formulation, preferably Pluronic F127.

In some embodiments, the scaffold material is an extracellular matrix material. In some embodiments, the extracellular matrix material is gelatin. In some embodiments, the scaffold material is gelated by crosslinking with a solution comprising glutaraldehyde, transglutaminase, or other crosslinking enzymes or molecules, and/or wherein the scaffold material is thermally crosslinked.

In some embodiments, the steps of submerging the plurality of membranes in a solution comprising a scaffold material and gelating the scaffold material comprises: (a) providing a bottom mold (64) having a open top reservoir and configured with a vascular channel system inflow conduit structure (63) and vascular channel system outflow conduit structure (65) each having an interior lumen filled with a sacrificial material, wherein the reservoir is partially filled with a gelated scaffold material that partially embeds the vascular channel system inflow conduit structure and the vascular channel system outflow conduit structure, (b) providing a plurality of membranes in frames, (c) filling the bottom mold (64) open top reservoir with solution comprising the scaffold material, (d) placing a frame on top of the bottom mold so that the membrane in the frame contacts the solution, (e) gelating the solution and then removing the frame from the membrane, (f) placing a spacer (62) having an interior volume around the top of the membrane, (g) filling the interior volume of the spacer with solution comprising the scaffold material, (h) placing a frame on top of the spacer so that the membrane in the frame contacts the solution, (i) optionally repeating steps e. through h. one or more times to add additional membranes to the apparatus, (j) placing a spacer (57) on top of the last membrane configured with a filtration channel system outflow conduit structure (56) having an interior lumen filled with a sacrificial material, (k) filling the interior volume of the spacer (57) with solution comprising the scaffold material and gelating the solution, (l) adding a shaft filled with sacrificial material to the gelated solution that fluidly connects the first end of the plurality of membranes to the vascular channel system inflow conduit structure (63), adding a shaft filled with sacrificial material to the gelated solution that fluidly connects the second end of the plurality of membranes to the vascular channel system outflow conduit structure (65), and adding a shaft filled with sacrificial material to the gelated solution that fluidly connects the third end of the plurality of membranes to the filtration channel system outflow conduit structure (56), and (m) removing the sacrificial material from the construct.

In some embodiments, the method of generating an apparatus further comprises adding cells to one or more segments of a vascular channel system and/or filtration channel system. In some embodiments, the cells are added to a segment by (a) filling the vascular channel system and filtration channel system with a fluid, (b) placing the cells in a first volume of fluid about equal to the volume of fluid in the channel system of a target segment, (c) adding the first volume to apparatus through a first fluid supply or fluid outlet in fluid communication with the target segment, and (d) adding a second volume of fluid about equal to the volume of fluid contained between the target segment and the first fluid supply or fluid outlet and/or removing a third volume of fluid about equal to the volume of fluid contained between the target segment and a second fluid supply or fluid outlet in fluid communication with the first fluid supply or fluid outlet.

In some embodiments, the cells are added to each functional unit of the apparatus. In some embodiments, the cells are added to each segment of each functional unit of the apparatus (e.g., both or either of the vascular channel system and filtration channel system located in each segment). In some embodiments, cells are added to both the vascular channel system and the filtration channel system. The cells are not limited and may be any cell described herein.

Some aspects of the disclosure are related to a membrane comprising a biologic or synthetic matrix material and having pores having a diameter of about 1 µM to 15 µM. In some embodiments, the biologic or synthetic matrix material comprising decellularized tissue, gelatin, gelatin composites, collagen, fibrin, hydrogel, hydrogel composites, chitosan, nitrocellulose, polylactic acid, or extra-cellular matrix. In some embodiments, the membrane has a thickness of about 0.1 µM to 100 µM. The membrane may be any thickness described herein and is not limited.

Some aspects of the disclosure are related to a method of generating the membrane described herein, comprising chemical or physical thin film deposition, atomization, spraying, electrospinning, dip coating, or gelation of a solution (i.e. membrane solution) comprising decellularized tissue, gelatin, gelatin composites, collagen, fibrin, hydrogel, hydrogel composites, chitosan, nitrocellulose, polylactic acid, or extra-cellular matrix that has been liquefied or homogenized, in a thin film layer followed by curing, crosslinking, polymerizing, drying, or gelating the solution to form a membrane layer. In some embodiments, the membrane solution further comprises a porogen homogenously mixed therein. The porogen is not limited and may be any porogen described herein. In some embodiments, the porogen is a self-assembling tri-block copolymer. In some embodiments, the self-assembling tri-block copolymer is a poloxamer formulation, preferably Pluronic F127 at a concentration of 1-40% wt in the membrane solution.

In some embodiments, the membrane solution further comprises one or more agents modifying the mechanical or biological properties of the membrane. In some embodiments, the one or more agents are selected from glycerin, sorbitol, propylene glycol, plasticizers, fibers or other longitudinal elements, and growth factors (e.g., encapsulated growth factors).

In some embodiments, the method of generating the membrane further comprises adding one or more additional membrane layers by the methods disclosed herein to the first membrane layer in order to create a membrane of mixed composition or architecture. In some embodiments, the two or more layers are generated from membrane solutions having different components, agents and/or concentrations.

In some embodiments, the membranes are treated to remove the porogen, thereby forming pores in the membrane. In some embodiments, the porogen material has a thermally reversible gelation property or can be dissolved in non-polar solvent. In some embodiments, the porogen material is Pluronic F127 and is removed by treatment with a non-polar solvent (e.g., isopropanol).

In some embodiments, the membrane solution comprises 3-35 wt % of gelatin or a gelatin-polymer composite.

In some embodiments, the thin film layer may be dried, gelled, crosslinked, or otherwise solidified and removed from the substrate. In some embodiments, the thin film layer is crosslinked with a solution comprising glutaraldehyde, transglutaminase, or other crosslinking enzymes or molecules. In some embodiments, the concentration of crosslinking agent is about 0.01-5 g per 10 g of scaffold material.

(41) Vascular side channel; (42) Matrix membrane; (43) Filtrate side channel; (44) Main vascular channel.

Figure 8:
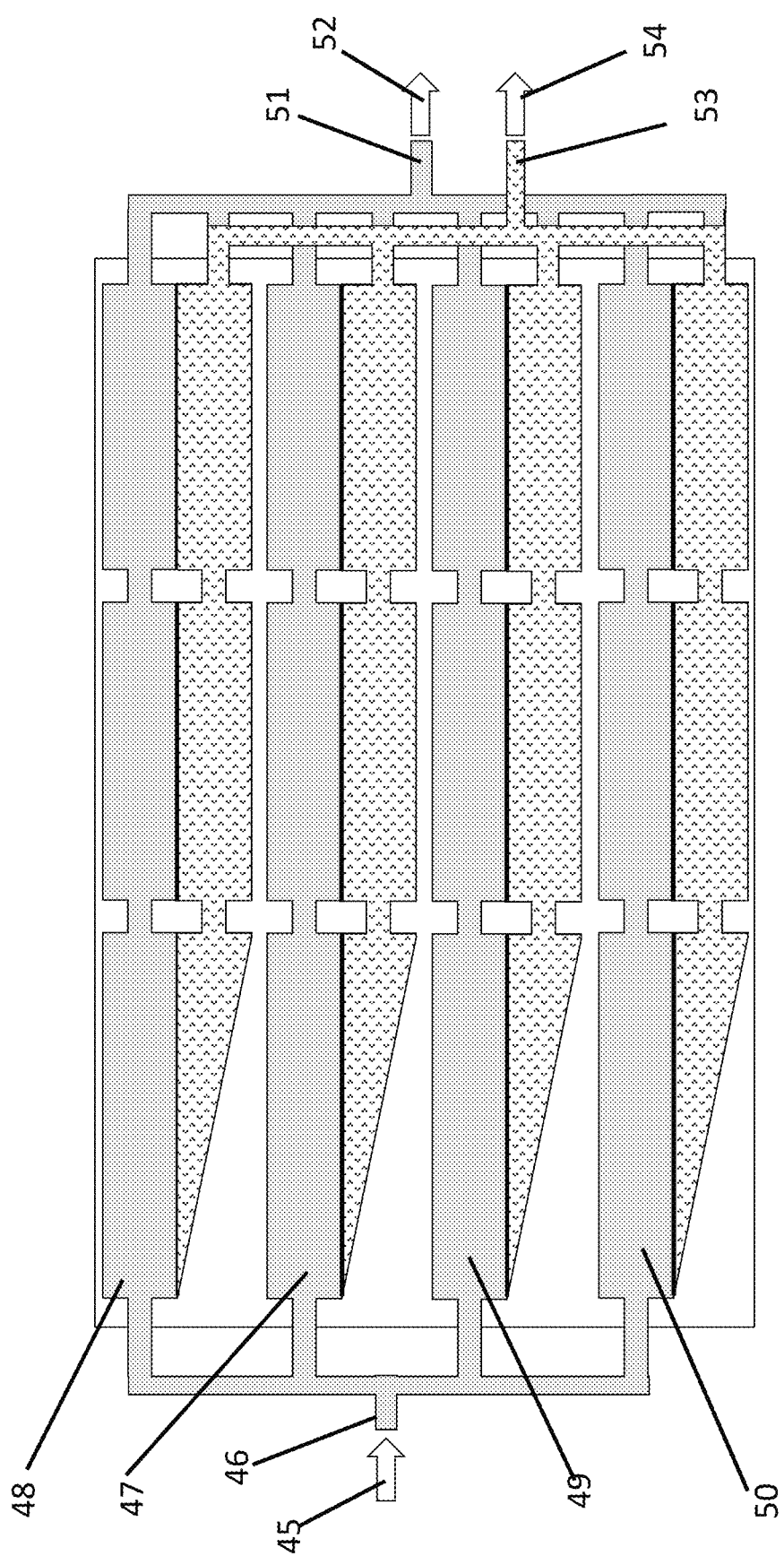

FIG. 8 shows a schematic of a stack of functional units in an IABBP device that are perfused and drained in parallel. (45) Graft Blood inflow; (46) Graft Blood inlet conduit; (47) Stacked functional unit; (48) Stacked functional unit; (49) Stacked functional unit; (50) Stacked functional unit; (51) Graft Blood outflow conduit; (52) Graft Blood outflow; (53) Graft Filtrate outflow conduit; (54) Graft Filtrate outflow.

Figure 9:
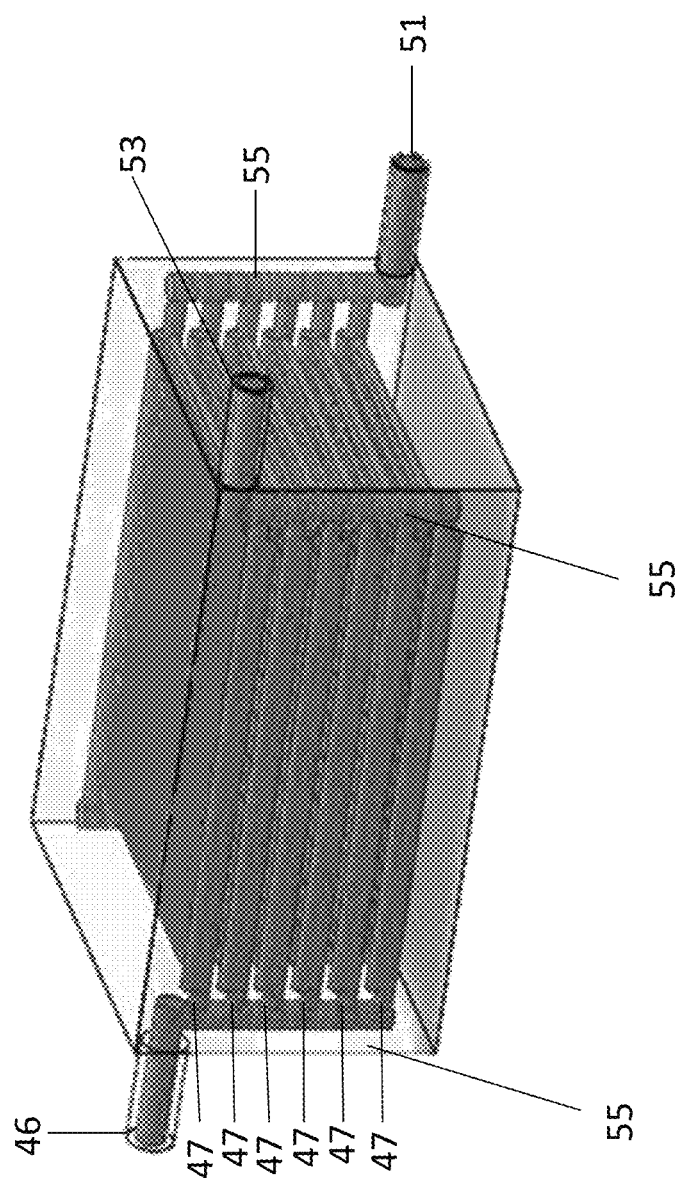

FIG. 9 shows a three-dimensional rendering of a multi-layered IABBP device. Five layers of functional units are layered and connected in parallel to be perfused with blood and produce a filtrate that is drained via the filtrate drainage conduit. (46) Graft blood inlet conduit; (51) Graft blood outlet conduit; (53) Graft filtrate outflow conduit; (47) Stacked functional units; (55) Connection channel.

Figure 10:
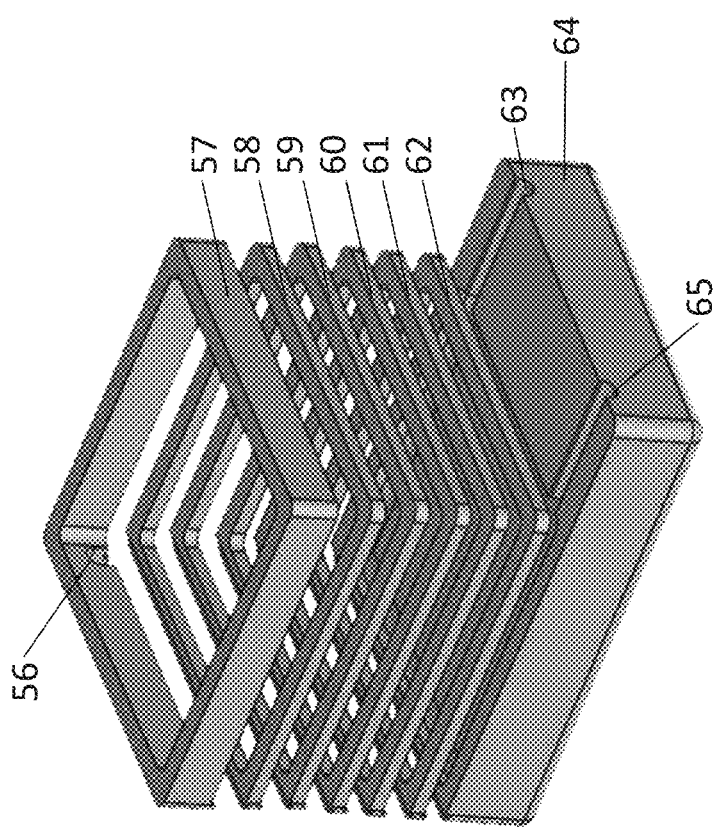

FIG. 10 shows a three-dimensional rendering of a manufacturing mold to generate a multilayered IABBP device. The base mold and the top mold accommodate vascular and filtrate conduits. Each cassette enables the addition of an embedding material and supports a patterned membrane. (56) Notch for top conduit; (57) Top mold; (58) Spacer 1; (59) Spacer 2; (60) Spacer 3; (61) Spacer 4; (62) Spacer 5; (63) Recessed groove for bottom conduit 1; (64) Bottom mold; (65) Recessed groove for bottom conduit 2.

Figure 11:
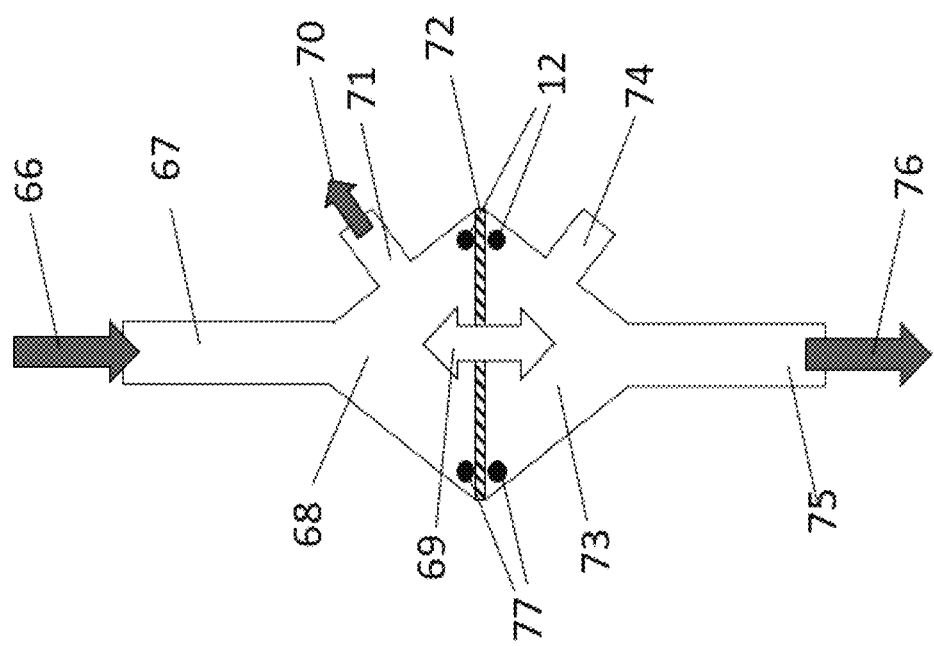

FIG. 11 shows a schematic of a membrane Testing Apparatus and its components. (66) Plasma or blood inflow; (67) Plasma or blood inflow port; (68) Top chamber—vascular space; (69) Solute and fluid exchange; (70) Plasma or blood outflow; (71) Plasma or blood outflow port; (72) Membrane; (73) Bottom chamber; (74) Bottom mold; (75) Filtrate drainage port; (76) Filtrate drainage; (77) O-rings.

Figure 12:
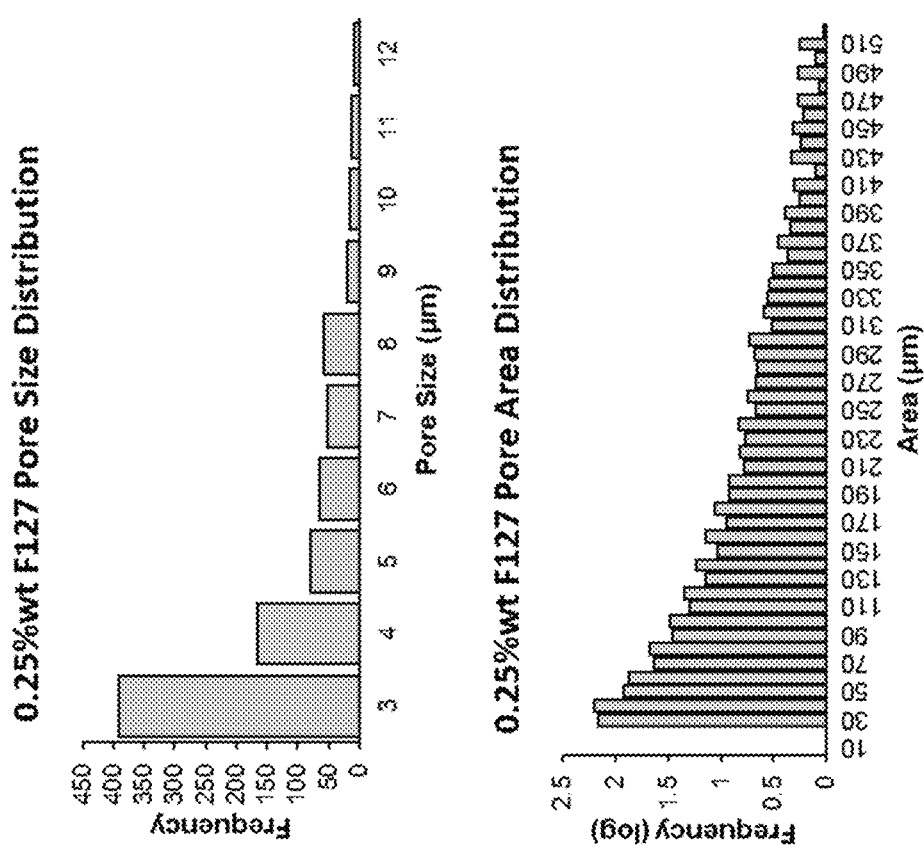

FIG. 12 shows pore size and area distribution of a membrane manufactured from a mixture of gelatin and 0.25% Pluronic F127.

Figure 13:
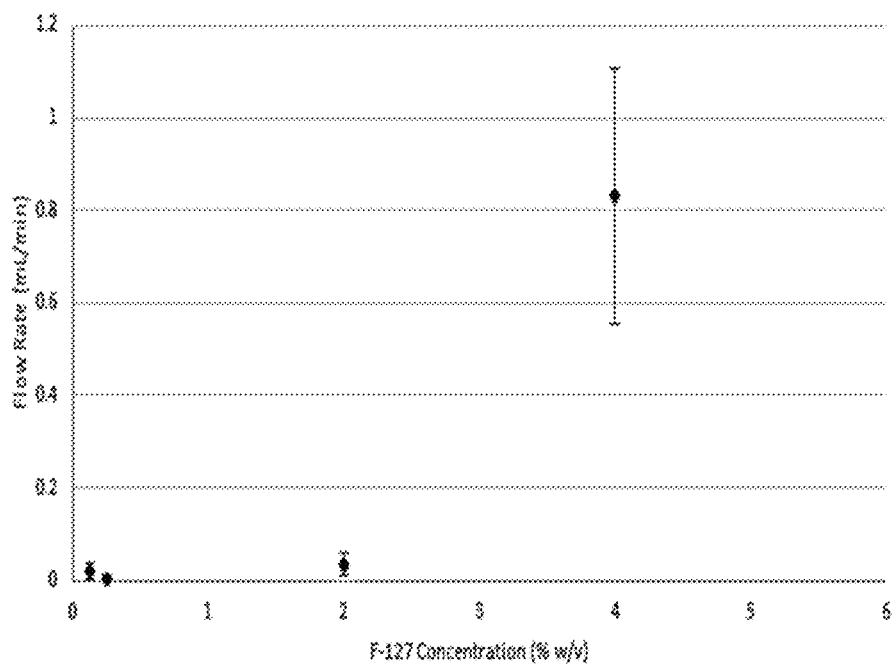
Figure 13:
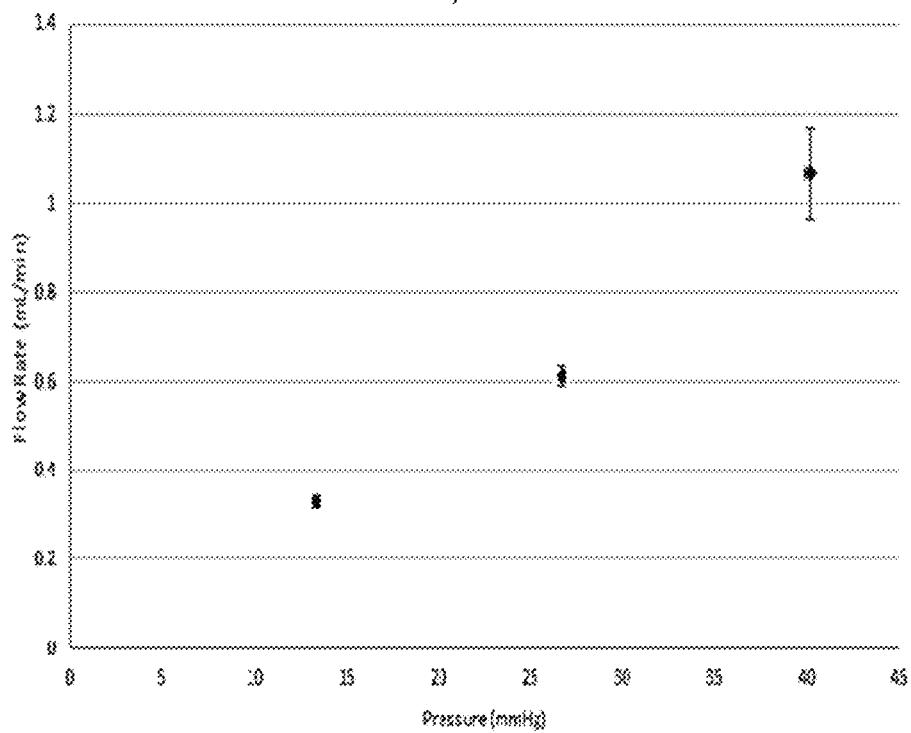

FIG. 13 (top panel) shows Pluronic F127 concentration versus flow rate. FIG. 13 (bottom panel) shows fluid pressure versus flow rate.

DETAILED DESCRIPTION OF THE INVENTION

Biological Fluid Purification

Some aspects of the disclosure are related to an apparatus for adaptive biologic blood purification (AIBBP) comprising a functional unit comprising (1) a membrane comprising a vascular surface and a filtration surface; (2) a vascular channel system comprising a first luminal space, adhered to and in fluid communication with the vascular surface of the membrane, and comprising a first end configured to connect in fluid communication to a fluid supply and a second end configured to connect in fluid communication to a filtered fluid outlet; and (3) a filtration channel system comprising a second luminal space, adhered to and in fluid communication with the filtration surface of the membrane, and comprising a third end configured to connect in fluid communication to a filtrate outlet. The vascular channel system and the filtration channel system are in fluid communication with each other across the membrane. Further, the functional unit further comprises at least three segments, including at least a filtration segment configured to provide ultrafiltration producing a primary ultrafiltrate, connecting to a tubular segment configured to provide reabsorption producing a secondary ultrafiltrate, connecting to a ductal segment configured to provide concentration producing a tertiary ultrafiltrate; and the membrane comprises three membrane segments including at least a filtration membrane segment, a tubular membrane segment and a ductal membrane segment.

In some embodiments, the filtration membrane segment enables production of a filtrate from the first luminal space in the vascular channel system to the second luminal space of the filtration channel system. In some embodiments, the tubular membrane segment enables solute and water exchange and/or diffusion between the vascular channel system and the filtration channel system. In some embodiments, the ductal membrane segment enables transfer of water and solutes from the filtration channel system to the vascular channel system.

In some embodiments, the functional unit comprises at least one biological fluid inflow conduit in fluid communication with the first end of the vascular channel system and the first luminal space and at least one biological fluid outflow conduit in fluid communication with the second end of the vascular channel system and the first luminal space. In some embodiments, the functional unit comprises at least one filtrate outflow conduit in fluid communication with the third end of the filtration channel system and the second luminal space. In some embodiments, the functional unit further comprises one or more vascular segment conduits interconnecting the filtration segment, the tubular segment and the ductal segment of the vascular channel system and the first luminal space and one or more filtration segment conduits interconnecting the filtration segment, the tubular segment and the ductal segment of the filtration channel system and the second luminal space.

In some embodiments, the at least one biological fluid inflow conduit is in fluid communication with an arterial conduit, the at least one biological fluid outflow conduit is in fluid communication with a vascular conduit, and the at least one filtrate outflow conduit is in fluid communication with a drain conduit.

In some embodiments, the membrane comprises a porous membrane that comprises pores disposed to interconnect the vascular surface and the filtration surface. In some embodiments, the pores have a diameter of less than about 15 μm, 14 μm, 13 μm, 12 μm, 11 μm, 10 μm, 9 μm, 8 μm, 7 μm, 6 μm, 5 μm, 4 μm, 3 μm, 2 μm, or 1 μm. In some embodiments, the pores have an average or mean diameter of about 15 μm, 14 μm, 13 μm, 12 μm, 11 μm, 10 μm, 9 μm, 8 μm, 7 μm, 6 μm, 5 μm, 4 μm, 3 μm, 2 μm, or 1 μm. In some embodiments, the membrane containing pores has a flow rate when subjected to a fluid pressure of 40 mmHg of about 0.2 to 2.0 mL/min, about 0.5 to 1.5 mL/min, or about 0.8 to 1.2 ml/min. In some embodiments, the membrane is manufactured by a process comprising mixing an extracellular matrix material (e.g., gelatin) with a porogen (pore forming agent). In some embodiments, the pore forming agent is Pluronic F127. In some embodiments, the membrane is manufactured by a process disclosed herein.

In some embodiments, the membrane is as described in PCT Application No. PCT/US2017/67141, filed Dec. 18, 2017, incorporated herein by reference in its entirety. In some embodiments, the membrane may be constructed from any biologic, synthetic, or composite material suitable for thin film deposition and capable of maintaining mechanical viability and barrier integrity between compartments. This membrane may contain pores, slits, surface roughness, or other functional characteristics imparted during fabrication using techniques known to the art designed to improve function, biocompatibility, or other qualities of the membrane. The membrane may be manufactured from biologic, synthetic, or composite materials such as collagen, gelatin, other hydrogels, cellulose, or other materials that can be deposited in a thin film and subsequently crosslinked, dried, gelled, cured, or otherwise stabilized to form a cohesive and mechanically stable membrane. This membrane may undergo further treatment or manipulation to provide enhanced function or mechanics. This membrane may be of uniform or varying thicknesses in the range of 0.01 µm to 100 µm or greater. In some embodiments, the membrane has a thickness of about 0.1 µM to about 100 µM, of about 0.1 µM to about 100 µM, of about 0.5 µM to about 50 µM, of about 1.0 µM to about 40 µM, of about 5.0 µM to about 30 µM, or of about 10 µM to about 20 µM, or any range therebetween. In some embodiments, the membrane has a thickness of about 10 µM or less. In some embodiments, the membrane has a thickness of about 1-8 µM. In some embodiments, the membrane has a thickness of about 5 µM or less.

In some embodiments, the biocompatible extracellular matrix membrane comprises fibers, nano-fibers, or other longitudinal elements. In some embodiments, the fibers, nano-fibers, or other longitudinal elements are bonded to an exterior surface of the membrane. In some embodiments, the fibers, nano-fibers, or other longitudinal elements increase or modulate the mechanical strength of the membrane. In some embodiments, the fibers, nano-fibers, or other longitudinal elements form a mesh (e.g., an ordered mesh, a disordered mesh) or are orientated in substantially a single direction or substantially in two directions (e.g., a mesh).

In some embodiments, the fibers, nano-fibers, or other longitudinal elements increase the mechanical strength of the membrane, or a portion thereof, by at least about 10%, 20%, 30%, 40%, 50%, 60%, 70%, 80%, 90%, 99% or more as compared to an identical membrane without the fibers, nano-fibers, or other longitudinal elements. In some embodiments, the fibers, nano-fibers, or other longitudinal elements increase the mechanical strength of the membrane, or a portion thereof, by at least about 1.1-fold, 1.5-fold, 2-fold, 3-fold, 5-fold, 10-fold, or more as compared to an identical membrane without the fibers, nano-fibers, or other longitudinal elements. In some embodiments, the fibers, nano-fibers, or other longitudinal elements are evenly distributed throughout the membrane and provide homogenous mechanical strengthening. In some embodiments, the fibers, nano-fibers, or other longitudinal elements are heterogeneously distributed in the membrane and provide heterogeneous mechanical strengthening. In some embodiments, the fibers, nano-fibers, or other longitudinal elements provide resistance to cellular infiltration and maintain separation of the distinct cell populations on each side of the membrane. In some embodiments, the fibers, nano-fibers, or other longitudinal elements form a mesh and provide resistance to cellular infiltration and maintain separation of the distinct cell populations on each side of the membrane.

Fibers, nano-fibers, and other longitudinal elements disclosed herein can be made from a variety of materials, including (but not limited to) Dyneema®, an extremely strong polyethylene manufactured by DSM High Performance Fibers, a subsidiary of DSM N.V. The fibers can also be combined with fibers or wires of other materials, such as Nitinol (a version of shape memory nickel-titanium alloy), to help control the expanded shape of the filter. Other viable materials for use as fibers, nano-fibers, and other longitudinal elements include those known in the fiber art, such as carbon, glass, ceramic, metals and metal alloys (including the aforementioned Nitinol), natural and synthetic polymers (including ultra high molecular weight highly oriented polymers and silk) or combinations thereof. In some embodiments, the fibers, nano-fibers, or other longitudinal elements comprise silk or a polymer (e.g., polycarbonate). In some embodiments, the Fibers, nano-fibers, or other longitudinal elements form a mesh (e.g., polycarbonate mesh). Moreover, the fibers, nano-fibers, and other longitudinal elements can be made of a monofilament or multi-filament, and can be configured to have all kinds of cross sections and orientations. The fibers can be made of round, flat or different shaped monofilaments or multi-filaments. In some embodiments, the fibers are non-immunogenic.

In some embodiments, the membrane comprises, consists essentially of, or consists of a biocompatible extracellular matrix membrane separating the vascular channel system from the filtration channel system. In some embodiments, the biocompatible extracellular matrix membrane comprises a collagen membrane with a thickness of about 0.1-10 micrometers (e.g., 0.3-10 µm) that supports cell adhesion on both the vascular surface and the filtration surface of the collagen membrane.

In some embodiments, the biocompatible extracellular matrix membrane is embedded into a matrix material (i.e., a scaffold material). In some embodiments, the scaffolds comprise hydrogels such as gelatin, PLA, chitosan, composites of hydrogels or other hydrogel materials and composites of various concentrations and compositions. In some embodiments, varying the hydrogel materials and composites of various concentrations and compositions enable tuning of mechanical and biological properties of the scaffold which can enhance and further specialize tissue constructs for desired biological applications. In some embodiments, the scaffold can comprise an addition of glycerin, sorbitol, propylene glycol, or other plasticizers into gelatin or gelatin composite hydrogels. The composition of the scaffold is not limited and may be any suitable scaffold material known in the art.

In some embodiments, the apparatus comprises at least one biological fluid inflow conduit in fluid communication with the first end of the vascular channel system and the first luminal space and at least one biological fluid outflow conduit in fluid communication with the second end of the vascular channel system and the first luminal space, and wherein the functional unit comprises at least one filtrate outflow conduit in fluid communication with the third end of the filtration channel system and the second luminal space.

In some embodiments, the vascular and filtration channel systems are manufactured by the methods disclosed in PCT Application No. PCT/US2017/67141, filed Dec. 18, 2017, incorporated herein by reference in its entirety. Briefly, a sacrificial material is overlaid on the membrane, followed by scaffold material; then the sacrificial material is removed, leaving a luminal space bounded by the scaffold material and the membrane. The membrane is then flipped over, a sacrificial material is overlaid on the membrane, followed by scaffold material; then the sacrificial material is removed, leaving a second luminal space bounded by the scaffold material and the membrane. In some embodiments, the vascular and filtration channel systems are partially or fully in fluid communication across the membrane (e.g., are mirror images opposite of each other across the membrane). In some embodiments, the area of membrane across which the first and second luminal spaces are in fluid communication across the membrane is at least 30 cm$^2$, at least 60 cm$^2$, at least 90 cm$^2$, at least 100 cm$^2$, at least 150 cm$^2$, at least 200 cm$^2$, at least 250 cm$^2$, at least 300 cm$^2$, at least 450 cm$^2$, at least 600 cm$^2$, at least 800 cm$^2$, at least 1000 cm$^2$, or at least 1200 cm$^2$ or more. In some embodiments, at least 10%, 20%, 30%, 40%, 50%, 60%, 70%, 80%, 90%, 95%, 99%, or more of the first and/or second luminal space is in fluid communication across the membrane with the other luminal space.

In some embodiments, the at least one biological fluid inflow conduit is in fluid communication with an arterial conduit. In some embodiments, the at least one biological fluid outflow conduit is in fluid communication with a vascular conduit. In some embodiments, the at least one filtrate outflow conduit is in fluid communication with a drain conduit.

In some embodiments, the apparatus produces a filtrate and/or an ultrafiltrate that is drained, using a drain conduit into an extracorporeal collection system (e.g., waste container). In some embodiments, the filtrate and/or ultrafiltrate is drained into a plumbing system or sewage treatment system. In some embodiments, the filtrate and/or ultrafiltrate is drained, using a drain conduit into a patient bladder or digestive system.

In some embodiments, the vascular channel system comprises vascular channel walls lined with endothelial cells and/or epithelial cells and/or the filtration channel comprises filtration channel walls lined with endothelial cells and/or epithelial cells. In some embodiments, the cells are at confluence on the vascular channel walls and/or the filtration channel walls. In some embodiments, the vascular channel walls and/or the filtration channel walls comprise at least $2\times10^6$ cells. In some embodiments, the vascular channel walls and/or the filtration channel walls comprise at least $1\times10^7$ cells. In some embodiments, the vascular channel walls and/or the filtration channel walls comprise at least $2\times10^7$ cells. In some embodiments, the cells are on at least 30 cm$^2$, at least 60 cm$^2$, at least 90 cm$^2$, at least 100 cm$^2$, at least 150 cm$^2$, at least 200 cm$^2$, at least 250 cm$^2$, at least 300 cm$^2$, at least 450 cm$^2$, at least 600 cm$^2$, at least 800 cm$^2$, at least 1000 cm$^2$, or at least 1200 cm$^2$ or more of the vascular channel walls and/or the filtration channel walls.

In some embodiments, the epithelial cell type is selected from prostate cells, mammary cells, hepatocytes, pancreatic islet cells including beta cells, pulmonary epithelial cells, kidney cells, bladder cells, stomach epithelial cells, large and small intestinal epithelial cells, urethral epithelial cells, testicular epithelial cells, ovarian epithelial cells, cervical epithelial cells, thyroid cells, parathyroid cells, adrenal cells, thymus cells, gall bladder cells, and pituitary cells. In some embodiments, the endothelial cell is a brain endothelial cell, a vascular endothelial cell, primary human peritubular capillary endothelial cell, iPSC derived endothelial cell, human umbilical cord endothelial cell, primary human renal medullary endothelial cell, human podocyte, or a human iPSC derived podocyte. In some embodiments, the cells are allogenic to a patient using the apparatus. In some embodiments, the cells are autologous to a patient using the apparatus. In some embodiments, the cells are from a cell line. In some embodiments, the cells are autologous stem cell derived cells. In some embodiments, the autologous stem cells are derived from induced pluripotent stem cells.

In some embodiments, the filtration segment of the vascular channel system comprises vascular channel walls lined with endothelial cells selected from primary human glomerular endothelial cells, induced pluripotent stem cell (iPSC) derived endothelial cells, and/or human umbilical cord endothelial cells.

In some embodiments, the cells are obtained from a kidney as described below in the section titled "Primary Cell Isolation from Discarded Kidneys" of the examples.

In some embodiments, the tubular segment of the vascular channel system comprises vascular channel walls (e.g., walls comprising scaffold material and membrane) lined with endothelial cells selected from primary human peritubular capillary endothelial cells, iPSC derived endothelial cells, and/or human umbilical cord endothelial cells.

In some embodiments, the ductal segment of the vascular channel system comprises vascular channel walls lined with endothelial cells selected from primary human renal medullary endothelial cells, iPSC derived endothelial cells, and/or human umbilical cord endothelial cells.

In some embodiments, the filtration segment of the filtration channel system comprises filtration channel walls lined with epithelial cells selected from primary human podoytes and/or human iPSC derived podocytes.

In some embodiments, the tubular segment of the filtration channel system comprises filtration channel walls (e.g., walls comprising scaffold material and membrane) lined with epithelial cells selected from primary human tubular epithelial cells and/or iPSC derived tubular epithelial cells.

In some embodiments, the ductal segment of the filtration channel system comprises filtration channel walls lined with epithelial cells selected from primary human tubular epithelial cells and/or iPSC derived tubular epithelial cells.

In some embodiments, the vascular channel system comprises a vascular channel diameter of between 1 mm and 10 µm. In some embodiments, the filtration channel system comprises a filtration channel diameter of between 1 mm and 10 µm. In some embodiments, the channel systems (e.g., the vascular channel system and/or filtration channel system) comprise more than one channel (e.g., at least 2, 3, 4, 5, 6, 7, 8, 9, 10, 11, 12, 13, 14, 15, 16, 17, 18, 19, 20, 25, 30, 40, 50, 100, 200, 500, 750, 1000, 2000, 10000 channels). In some embodiments, the channel system comprises a branching channel network having one or more branches with decreasing diameters (e.g., at least 1, 2, 3, 4, 5, 6, 7, 8, 9, 10, 11, 12, 13, 14, 15, 16, 17, 18, 19, 20, 25, 30, 40, 50, 100, 200, 500, 750, 1000, 2000, 10000 branches). In some embodiments, channel diameters can include, but not be limited to, about 10 cm, 5 cm, 2 cm, 1 cm, 500 mm, 250 mm, 100 mm, 50 mm, 10 mm, 5 mm, 1 mm, 500 µm, 50 µm, 10 µm, 5 µm, 3 µm, 1 µm, 0.5 µm, 0.1 µm, 0.05 µm, 0.02 µm, or 0.01 µm. In some embodiments, the vascular channel system and the filtration channel system are embedded in scaffold (e.g., biocompatible matrix material).

In some embodiments, the apparatus comprises a plurality of functional units, including the functional unit and additional functional units of a same configuration (see, e.g., FIG. 8), wherein each functional unit of the plurality of functional units has a first end of a vascular channel system and first luminal space in fluid communication with the at least one biological fluid inflow conduit; a second end of a vascular channel system and first luminal space in fluid communication with the at least one biological fluid outflow conduit, and a third end of a filtration channel system and second luminal space in fluid communication with a filtrate outflow conduit; wherein each first end of the plurality of functional units connects individually and in parallel to one of a plurality of manifold ports of the at least one biological fluid inflow conduit; wherein each second end of the plurality of functional units connects individually and in parallel to one of a plurality of manifold ports of the at least one biological fluid outflow conduit; and wherein each third end of the plurality of functional units connects individually and in parallel to one of a plurality of manifold ports of the at least one filtrate outflow conduit. In some embodiments, the plurality of functional units, including the functional unit and the additional functional units of a same configuration, are stacked in parallel layers of functional units.

In some embodiments, the at least one biological fluid inflow conduit comprises a blood inlet conduit configured to transport a Blood inflow, the at least one biological fluid outflow conduit comprises a blood outflow conduit configured to transport a blood outflow, and parallel layers of functional units configured for biologic blood purification.

In some embodiments, the filtration segment of the filtration channel system is configured to provide ultrafiltration producing a primary ultrafiltrate, the tubular segment is configured to provide reabsorption producing a secondary ultrafiltrate flow by solute and water absorption, and the ductal segment is configured to provide concentration producing a tertiary ultrafiltrate flow by water absorption.

In some embodiments, the apparatus is configured for extracorporeal operation in a sterile, heated enclosure. In some embodiments, blood is delivered to the apparatus with a mechanical pump. In some embodiments, the apparatus is disposed within a capsule, and sized and configured for placement within a human body to replace or augment a tissue or organ function (e.g., a liver and/or kidney function).

Some aspects of the disclosure are related to a method of treating a patient having an insufficient kidney or liver function comprising fluidly connecting the apparatus described herein to the circulation system of the patient and passing patient blood through the vascular channel system of the apparatus from the filtration member segment to the tubular member segment, from the tubular member segment to the ductal member segment, and from the ductal member segment back into the circulation system of the patient. In some embodiments, the apparatus comprises a plurality of functional units as described herein and the patient blood is passed through the plurality of functional units. In some embodiments, the patient blood is passed in parallel through the functional units. In some embodiments, the patient blood is passed through the functional units in series. In some embodiments, the apparatus is implanted in the patient. In some embodiments, ultrafiltrate produced by the apparatus is delivered extracorporeal to the patient. In some embodiments, the ultrafiltrate produced by the apparatus is delivered to the bladder of the patient.

In some embodiments, the apparatus is extracorporeal to the patient. For example, the apparatus may be stationary or the apparatus may be configured to be carried by the patient such as in a backpack or waist pack, allowing the patient to be mobile while using the apparatus.

In some embodiments, the apparatus is extracorporeal to the patient and configured for use in peritoneal dialysis (e.g., as a peritoneal dialysis adjunct device). Peritoneal dialysis (PD) is a type of dialysis that uses the peritoneum in a patient's abdomen as the membrane through which fluid and dissolved substances are exchanged with the blood. PD is used to remove excess fluid, correct electrolyte problems, and remove toxins in those with kidney failure. Continuous Ambulatory Peritoneal Dialysis (CAPD) requires the patient to add and remove dialysate thorough a catheter in the abdomen multiple times per day. During periods when the dialysate is present in the peritoneal cavity, the patient may move about (i.e., ambulate). However, the longer the dialysate is present in the peritoneal cavity, the less effective the dialysate becomes at removing wastes as the dialysate nears equilibrium. In continuous flow peritoneal dialysis (CFPD), the dialysate is continuously added and removed from the patient's peritoneal cavity, also usually during sleep. CFPD requires large dialysate reservoirs and a total dialysate volume of 6-12 liters per sleep period.

In some embodiments, the apparatus is configured to be connected to the peritoneal cavity such that fluid from the peritoneal cavity is circulated through the apparatus (e.g., via pumps or the like) and at least a portion thereof returned to the peritoneal cavity. In some embodiments, the apparatus is configured to remove a portion of the fluid from the peritoneal cavity as waste fluid. In some embodiments, the apparatus comprises a waste outlet or waste storage receptacle that, optionally, may be drained or swapped (e.g., hot swapped during operation) for a new waste storage receptacle when necessary. In some embodiments, the apparatus is part of a peritoneal dialysis system (CAPD and/or CFPD) comprising pumps that circulate dialysate solution from the peritoneal cavity of a patient through the apparatus and back to the peritoneal cavity, thereby removing toxins and/or excess fluid from the dialysis solution. In some embodiments, use of the apparatus reduces the volume of dialysis fluid needed for effective dialysis (e.g., by at least 10%, 25%, 50%, or more). In some embodiments, the use of the apparatus increases the intervals between exchange of dialysis fluid in CAFD (e.g., by at least 10%, 25%, 50%, or more) without a loss in effectiveness as compared to CAFD without the apparatus. In some embodiments, the apparatus comprises kidney cells (e.g., cells from a discarded kidney as detailed in the Examples section below).

Methods of Manufacture

Some aspects of the disclosure are directed to a method of manufacturing the apparatus disclosed herein, comprising providing a plurality of membranes having a sacrificial material in the form of the vascular channel network on the vascular surface and having sacrificial material in the form of the filtration channel system on the filtration surface, submerging the plurality of membranes in a solution comprising a scaffold material (e.g. scaffold material in a sol state), gelating the scaffold material, and removing the sacrificial material to thereby form the luminal spaces of the vascular channel system and the filtration channel system as described herein.

In some embodiments, the plurality of membranes are each generated by chemical or physical thin film deposition, atomization, spraying, electrospinning, dip coating, or gelation of a solution (membrane solution) comprising decellularized tissue, gelatin, gelatin composites, collagen, fibrin, hydrogel, hydrogel composites, chitosan, nitrocellulose, polylactic acid, or extra-cellular matrix that has been liquefied or homogenized, in a thin film layer on a substrate followed by curing, crosslinking, polymerizing, drying, or gelating the solution to form a membrane layer.

In some embodiments, the membrane solution further comprises fibers, nanotubes, or other longitudinally oriented materials in order to provide improved mechanical properties. The fibers, nanotubes, or other longitudinally oriented materials are not limited and may be any fibers, nanotubes, or other longitudinally oriented materials disclosed herein. These fibers, nanotubes, or other longitudinally oriented materials can be mixed into the membrane solution prior to fabrication in order evenly distribute the fibers throughout the membrane. Alternatively, these fibers, nanotubes, or other longitudinally oriented materials can be deposited or integrated onto the membrane after fabrication through techniques such as electrospinning, 3D printing, or other techniques. In some embodiments, the membrane may be bonded to the fibers, nanotubes, or other longitudinally oriented materials. The fibers, nanotubes, or other longitudinally oriented materials may be homogenously distributed throughout the membrane or may be distributed in an organized manner to provide heterogenous mechanical properties for the membrane.

In some embodiments, the membrane solution further comprises a porogen homogenously mixed therein. In some embodiments, the porogen is in the form of micelles in the solution (e.g., the porogen is at a sufficient concentration in the solution to form micelles). In some embodiments, the porogen is incorporated in the solution via mixing or sonication. In some embodiments, the porogen is a self-assembling tri-block copolymer. In some embodiments, the self-assembling tri-block copolymer is a poloxamer formulation. In some embodiments, the porogen is Pluronic F127. In some embodiments, the porogen is at a concentration of 1-40% wt. In some embodiments, the porogen is at a concentration of about 1% wt, about 2% wt, about 3% wt, about 4% wt, about 5% wt, about 6% wt, about 7% wt, about 8% wt, about 9% wt, about 10% wt, about 11% wt, about 12% wt, about 13% wt, about 14% wt, about 15% wt, about 16% wt, about 17% wt, about 18% wt, about 19% wt, about 20% wt, about 21% wt, about 22% wt, about 23% wt, about 24% wt, about 25% wt, about 26% wt, about 27% wt, about 28% wt, about 29% wt, about 30% wt, about 31% wt, about 32% wt, about 33% wt, about 34% wt, about 35% wt, about 36% wt, about 37% wt, about 38% wt, about 39% wt, or about 40% wt in the solution. Pore size in the generated membrane can be controlled by using various polymers, but also by varying concentration, solution characteristics, and processing techniques to control micelle size and aggregation. Various concentrations and compositions of sacrificial porogen material can allow for substantial opportunities for tuning of mechanical and biological properties including but not limited to porosity, pore size, permeability, sieving, filtration, and other functions which can enhance and further specialize tissue constructs for desired biological applications.

In some embodiments, the membrane solution further comprises one or more agents modifying the mechanical or biological properties of the one or more membranes. Examples of agents include but are not limited to glycerin, sorbitol, propylene glycol, or other plasticizers into gelatin or gelatin composite hydrogels (See, F. M. Vanina et al., *Food Hydrocolloids* 19, 899-907 (2005)). In some embodiments, the agents comprise growth factors (e.g., encapsulated growth factors). In some embodiments, the one or more agents are selected from glycerin, sorbitol, propylene glycol, plasticizers, fibers or other longitudinal elements, and encapsulated growth factors.

In some embodiments, the method of generating the membrane further comprises adding one or more additional membrane layers by the methods disclosed herein to the first membrane layer in order to create a membrane of mixed composition or architecture. In some embodiments, the two or more layers are generated from membrane solutions having different components, agents and/or concentrations.

In some embodiments, the membranes are treated to remove the porogen, thereby forming pores in the membrane. The sacrificial porogen material is passively or forcefully removed in conjunction with dissolution, a phase transition, reversing of thermal gelation, or other techniques know to the art. In some embodiments, the sacrificial material has a thermally reversible gelation property or can be dissolved in non-polar solvent.

In some embodiments, the porogen material is Pluronic F127 and is removed by treatment with a non-polar solvent (e.g., isopropanol).

In some embodiments, the membrane solution comprises 3-35 wt % of gelatin or a gelatin-polymer composite. In some embodiments, the solution comprises about 3% wt, about 4% wt, about 5% wt, about 6% wt, about 7% wt, about 8% wt, about 9% wt, about 10% wt, about 11% wt, about 12% wt, about 13% wt, about 14% wt, about 15% wt, about 16% wt, about 17% wt, about 18% wt, about 19% wt, about 20% wt, about 21% wt, about 22% wt, about 23% wt, about 24% wt, about 25% wt, about 26% wt, about 27% wt, about 28% wt, about 29% wt, about 30% wt, about 31% wt, about 32% wt, about 33% wt, about 34% wt, or about 35% wt of gelatin or a gelatin-polymer composite.

In some embodiments, the thin film layer may be dried, gelled, crosslinked, or otherwise solidified and removed from the substrate. In some embodiments, the thin film layer is crosslinked with a solution comprising glutaraldehyde, transglutaminase, or other crosslinking enzymes or molecules. In some embodiments, a crosslinking agent is added to the membrane solution, e.g., just prior to applying the solution in a thin film on a substrate. In some embodiments, the crosslinking agent is contacted with the thin film layer after contact with the substrate. In some embodiments, the concentration of crosslinking agent is about 0.01-5 g per 10 g of gelatin.

In some embodiments, the solution comprising a scaffold material comprises an extracellular matrix material. In some embodiments, the extracellular matrix material is gelatin.

In some embodiments, the scaffold material is gelated by crosslinking with a solution comprising glutaraldehyde, transglutaminase, or other crosslinking enzymes or molecules, and/or wherein the scaffold material is thermally crosslinked.

In some embodiments, the steps of submerging the plurality of membranes in a solution comprising a scaffold material and gelating the scaffold material comprises: (a) providing a bottom mold (64) having an open top reservoir and configured with a vascular channel system inflow conduit structure (63) and vascular channel system outflow conduit structure (65) each having an interior lumen filled with a sacrificial material, wherein the reservoir is partially filled with a gelated scaffold material that partially embeds the vascular channel system inflow conduit structure and the vascular channel system outflow conduit structure, (b) providing a plurality of membranes in frames, (c) filling the bottom mold (64) open top reservoir with solution comprising the scaffold material, (d) placing a frame on top of the bottom mold so that the membrane in the frame contacts the solution, (e) gelating the solution and then removing the frame from the membrane, (f) placing a spacer (62) having an interior volume around the top of the membrane, (g) filling the interior volume of the spacer with solution comprising the scaffold material, (h) placing a frame on top of the spacer so that the membrane in the frame contacts the solution, (i) optionally repeating steps e. through h. one or more times to add additional membranes to the apparatus, (j) placing a spacer (57) on top of the last membrane configured with a filtration channel system outflow conduit structure (56) having an interior lumen filled with a sacrificial material, (k) filling the interior volume of the spacer (57) with solution comprising the scaffold material and gelating the solution, (l) adding a shaft filled with sacrificial material to the gelated solution that fluidly connects the first end of the plurality of membranes to the vascular channel system inflow conduit structure (63), adding a shaft filled with sacrificial material to the gelated solution that fluidly connects the second end of the plurality of membranes to the vascular channel system outflow conduit structure (65), and adding a shaft filled with sacrificial material to the gelated solution that fluidly connects the third end of the plurality of membranes to the filtration channel system outflow conduit structure (56), and (m) removing the sacrificial material from the construct. In some embodiments, the method of manufacturing an apparatus as described herein comprises the method described in "Manufacturing of a multilayered device" in the examples below.

In some embodiments, the method of manufacturing the apparatus further comprises adding cells to one or more segments of a vascular channel system and/or filtration channel system. In some embodiments, the cells are added to each functional unit of the apparatus. In some embodiments, the cells are added to each segment of each functional unit of the apparatus (e.g., both or either of the vascular channel system and filtration channel system located in each segment). In some embodiments, cells are added to both the vascular channel system and the filtration channel system. The cells are not limited and may be any cell described herein.

In some embodiments, the cells are added to a segment by (a) filling the vascular channel system and filtration channel system with a fluid, (b) placing the cells in a first volume of fluid about equal to the volume of fluid in the channel system of a target segment, (c) adding the first volume to apparatus through a first fluid supply or fluid outlet in fluid communication with the target segment, and (d) adding a second volume of fluid about equal to the volume of fluid contained between the target segment and the first fluid supply or fluid outlet and/or removing a third volume of fluid about equal to the volume of fluid contained between the target segment and a second fluid supply or fluid outlet in fluid communication with the first fluid supply or fluid outlet. In some embodiments, the cells are added (e.g., seeded) by the method described in the examples contained herein.

Membranes Comprising Pores and Methods of Manufacture Thereof

Some aspects of the disclosure are related to a membrane comprising a biologic or synthetic matrix material and having pores having a diameter of about 1 μM to 15 μM. In some embodiments, the biologic or synthetic matrix material comprising decellularized tissue, gelatin, gelatin composites, collagen, fibrin, hydrogel, hydrogel composites, chitosan, nitrocellulose, polylactic acid, or extra-cellular matrix. In some embodiments, the membrane may comprise any extracellular matrix material or scaffold material described herein. In some embodiments, the membrane has a thickness of about 0.1 μM to 100 μM. The membrane may be any thickness described herein and is not limited.

Some aspects of the disclosure are related to a method of generating the membrane described herein, comprising chemical or physical thin film deposition, atomization, spraying, electrospinning, dip coating, or gelation of a solution (i.e. membrane solution) comprising decellularized tissue, gelatin, gelatin composites, collagen, fibrin, hydrogel, hydrogel composites, chitosan, nitrocellulose, polylactic acid, or extra-cellular matrix that has been liquefied or homogenized, in a thin film layer followed by curing, crosslinking, polymerizing, drying, or gelating the solution to form a membrane layer. The method of generating (i.e., manufacturing) the membrane is not limited and may be any method described herein or known in the art. In some embodiments, the membrane solution further comprises a porogen homogenously mixed therein. The porogen is not limited and may be any porogen described herein. In some embodiments, the porogen is a self-assembling tri-block copolymer. In some embodiments, the self-assembling tri-block copolymer is a poloxamer formulation, preferably Pluronic F127 at a concentration of 1-40% wt in the membrane solution. The concentration porogen in the membrane solution is not limited and may be any concentration disclosed herein.

In some embodiments, the membrane solution further comprises one or more agents modifying the mechanical or biological properties of the membrane. The one or more agents are not limited and may be any agent modifying the mechanical or biological properties of the membrane described herein. In some embodiments, the one or more agents are selected from glycerin, sorbitol, propylene glycol, plasticizers, fibers or other longitudinal elements, and growth factors (e.g., encapsulated growth factors).

In some embodiments, the method of generating the membrane further comprises adding one or more additional membrane layers by the methods disclosed herein to the first membrane layer in order to create a membrane of mixed composition or architecture. In some embodiments, the two or more layers are generated from membrane solutions having different components, agents and/or concentrations.

In some embodiments, the membranes are treated to remove the porogen, thereby forming pores in the membrane. The sacrificial porogen material is passively or forcefully removed in conjunction with dissolution, a phase transition, reversing of thermal gelation, or other techniques know to the art. In some embodiments, the sacrificial material has a thermally reversible gelation property or can be dissolved in non-polar solvent.

In some embodiments, the porogen material is Pluronic F127 and is removed by treatment with a non-polar solvent (e.g., isopropanol).

In some embodiments, the membrane solution comprises 3-35 wt % of gelatin or a gelatin-polymer composite. In some embodiments, the solution comprises about 3% wt, about 4% wt, about 5% wt, about 6% wt, about 7% wt, about 8% wt, about 9% wt, about 10% wt, about 11% wt, about 12% wt, about 13% wt, about 14% wt, about 15% wt, about 16% wt, about 17% wt, about 18% wt, about 19% wt, about 20% wt, about 21% wt, about 22% wt, about 23% wt, about 24% wt, about 25% wt, about 26% wt, about 27% wt, about 28% wt, about 29% wt, about 30% wt, about 31% wt, about 32% wt, about 33% wt, about 34% wt, or about 35% wt of gelatin or a gelatin-polymer composite.

In some embodiments, the thin film layer may be dried, gelled, crosslinked, or otherwise solidified and removed from the substrate. In some embodiments, the thin film layer is crosslinked with a solution comprising glutaraldehyde, transglutaminase, or other crosslinking enzymes or molecules. In some embodiments, a crosslinking agent is added to the membrane solution, e.g., just prior to applying the solution in a thin film on a substrate. In some embodiments, the crosslinking agent is contacted with the thin film layer after contact with the substrate. In some embodiments, the concentration of crosslinking agent is about 0.01-5 g per 10 g of gelatin.

In some aspects of the disclosure, the membrane is used in tissue or biological constructs incorporating a membrane (e.g., a basement membrane) fabricated in the manner described herein. In some embodiments, tissue or biological constructs containing membranes fabricated as described herein comprise hydrogels such as gelatin, collagen, PLA, chitosan, or composites of hydrogels or other hydrogel materials and compounds. Gelatin and gelatin-polymer composites of but not limited to 3-35 wt % may be employed using a variety of film deposition techniques. Various concentrations and compositions of sacrificial porogen material can allow for substantial opportunities for tuning of mechanical and biological properties including but not limited to porosity, pore size, permeability, sieving, filtration, and other functions which can enhance and further specialize tissue constructs for desired biological applications.

In some embodiments, the membranes described herein are modified via techniques such as divalent metal ion removal or other techniques known to the art in order to yield tunable mechanical and biological properties (See, Qi et al., *Scientific Reports* 4: 4706 (2013)).

In some embodiments of the methods of generating membranes described herein, a second polymer or hydrogel material providing a support matrix for the membrane material is generated. This second hydrogel or polymer may be constructed of similar material as the membrane or may be constructed of a complimentary hydrogel or polymer.

In some embodiments, the membrane is partially or fully constructed of gelatin or other hydrogel material that has been altered to be photo-curable using ultraviolet light of various wavelengths, such as gelatin methacrylate. Materials such as this, in varying concentrations can be created using published protocols or techniques know to the art.

One skilled in the art readily appreciates that the present invention is well adapted to carry out the objects and obtain the ends and advantages mentioned, as well as those inherent therein. The details of the description and the examples herein are representative of certain embodiments, are exemplary, and are not intended as limitations on the scope of the invention. Modifications therein and other uses will occur to those skilled in the art. These modifications are encompassed within the spirit of the invention. It will be readily apparent to a person skilled in the art that varying substitutions and modifications may be made to the invention disclosed herein without departing from the scope and spirit of the invention.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects of the invention where appropriate. It is also contemplated that any of the embodiments or aspects can be freely combined with one or more other such embodiments or aspects whenever appropriate. Where elements are presented as lists, e.g., in Markush group or similar format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. For example, any one or more active agents, additives, ingredients, optional agents, types of organism, disorders, subjects, or combinations thereof, can be excluded.

Where the claims or description relate to a composition of matter, it is to be understood that methods of making or using the composition of matter according to any of the methods disclosed herein, and methods of using the composition of matter for any of the purposes disclosed herein are aspects of the invention, unless otherwise indicated or unless it would be evident to one of ordinary skill in the art that a contradiction or inconsistency would arise. Where the claims or description relate to a method, e.g., it is to be understood that methods of making compositions useful for performing the method, and products produced according to the method, are aspects of the invention, unless otherwise indicated or unless it would be evident to one of ordinary skill in the art that a contradiction or inconsistency would arise.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately".

As used herein "A and/or B", where A and B are different claim terms, generally means at least one of A, B, or both A and B. For example, one sequence which is complementary to and/or hybridizes to another sequence includes (i) one sequence which is complementary to the other sequence even though the one sequence may not necessarily hybridize to the other sequence under all conditions, (ii) one sequence which hybridizes to the other sequence even if the one sequence is not perfectly complementary to the other sequence, and (iii) sequences which are both complementary to and hybridize to the other sequence.

"Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. It should also be understood that unless otherwise indicated or evident from the context, any product or composition described herein may be considered "isolated".

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

EXAMPLES

Example 1

Porous Membrane Manufacture

In step 1, a solution of gelatin, collagen, fibrin, or other biologic or synthetic matrix material is created.

In step 2, a solution containing a sacrificial porogen material is combined with the matrix solution created in step 1 and thoroughly mixed.

In step 3, the matrix-porogen solution is deposited onto a substrate through spin coating, dip coating, or other such thin film deposition techniques and allowed to dry, gel, or otherwise solidify. This deposition technique allows for fine control over film thickness.

In step 4, additional layers of similar or dissimilar composition are optionally deposited onto the first layer to create a composite or layered film. Alternatively, additional layers are deposited in a manner allowing for patterning or other spatial organization within the membrane.

In step 5, the sacrificial porogen material is removed through dissolution, degradation, or other destructive techniques leaving an empty space in the thin film that serves as a pore.

Figure 1:
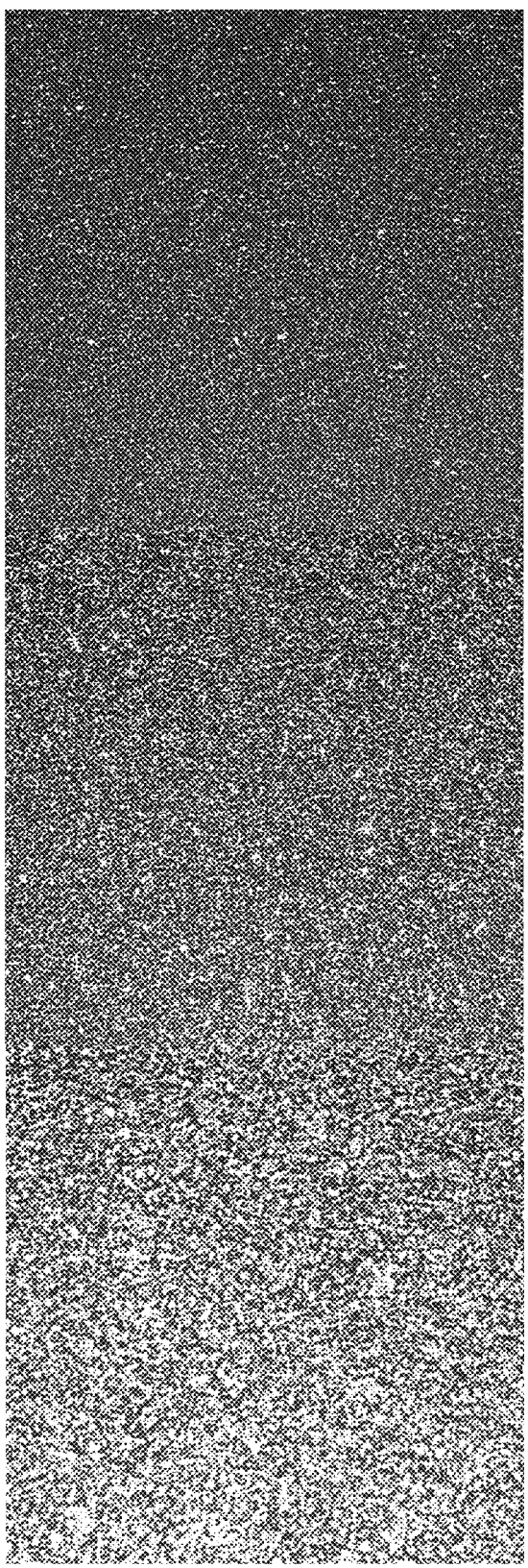
FIG. 1 shows microscopic imaging of thin films fabricated with variable amounts of sacrificial porogen material in order to facilitate control over porosity and pore size.

In one example of this invention, the sacrificial porogen material is composed of self-assembling tri-block copolymers (Pluronic) such as F127 or other poloxamer formulations that form micelles above a specific concentration. These micelles are incorporated into the matrix solution by mixing, sonication, or other methods to produce a homogenously disperse sacrificial porogen within the bulk matrix solution. Pore size can be controlled by using various polymers, but also by varying concentration, solution characteristics, and processing techniques to control micelle size and aggregation, as depicted in FIG. 1.

Figure 2:
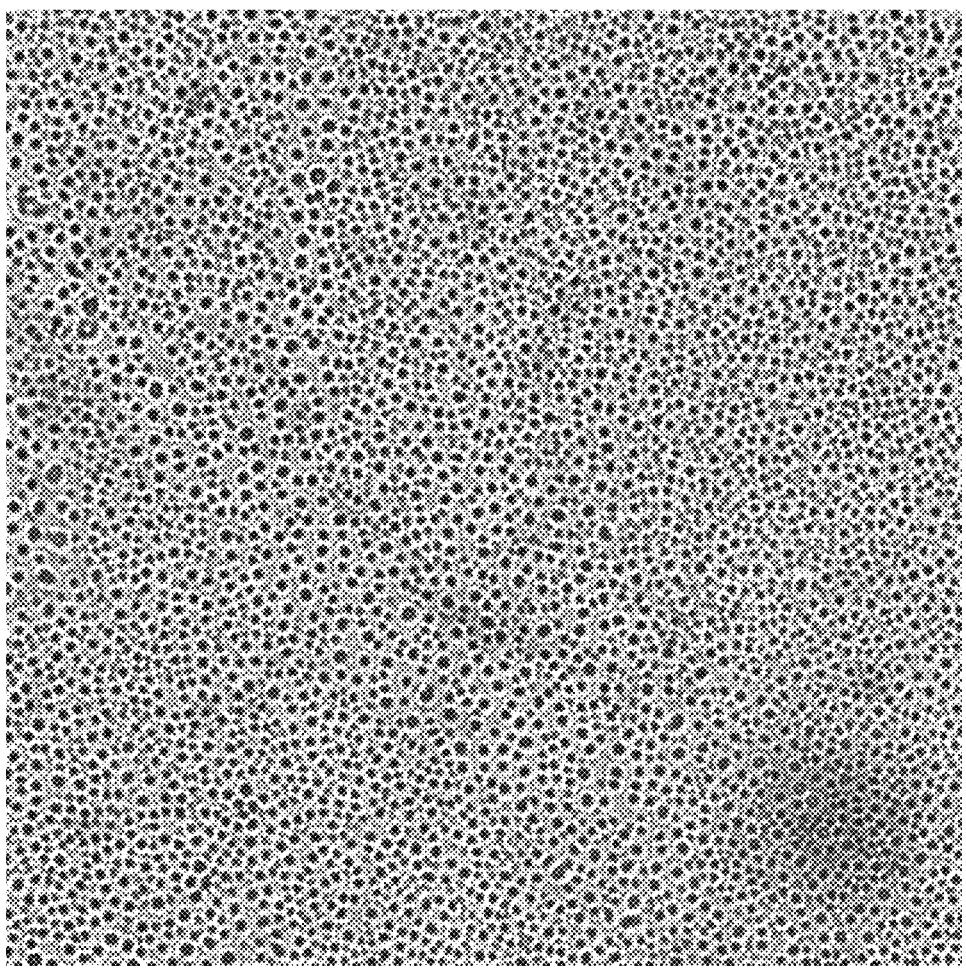
FIG. 2 shows microscopic imaging of thin films fabricated with a sacrificial porogen that has subsequently been removed to produce a porous thin film membrane.
Figure 3:
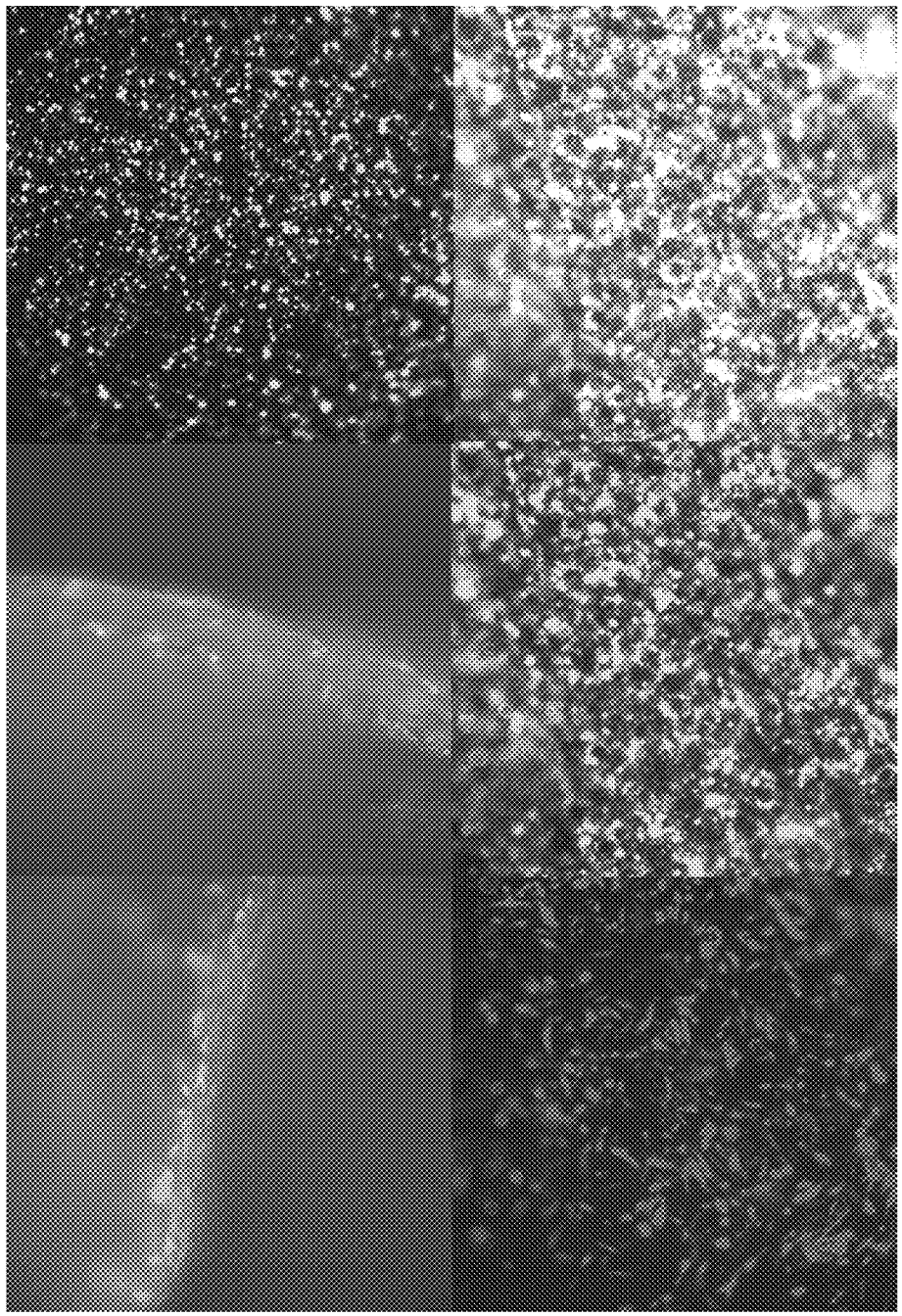
FIG. 3 shows a porous thin film membrane which has been seeded with layers of fluorescently marked endothelial and epithelial cells on opposing sides of the membrane.

This matrix-porogen solution is then subsequently deposited onto a substrate through spin coating or other thin film deposition techniques, and depending on technique and parameters film thickness may range anywhere from 0.1-100-μm. This film may be dried, gelled, crosslinked, or otherwise solidified and removed from the substrate. Once removed from the substrate, the sacrificial porogen material is passively or forcefully removed in conjunction with dissolution, a phase transition, reversing of thermal gelation, or other techniques know to the art, creating an open pore structure in the film. FIG. 2 depicts one such example of this type of film.

Specific examples of applications of this invention include tissue or biological constructs incorporating a basement membrane fabricated in the manner described. Additional examples include tissue or biological constructs containing membranes fabricated as described using hydrogels such as gelatin, collagen, PLA, chitosan, or composites of hydrogels or other hydrogel materials and compounds. Gelatin and gelatin-polymer composites of but not limited to 3-35 wt % may be employed using a variety of film deposition techniques. Various concentrations and compositions of sacrificial porogen material can allow for substantial opportunities for tuning of mechanical and biological properties including but not limited to porosity, pore size, permeability, sieving, filtration, and other functions which can enhance and further specialize tissue constructs for desired biological applications.

Additional examples of the invention include membranes as described in the previous examples, containing hydrogels, polymers, and compounds of materials which have been modified via techniques such as divalent metal ion removal or other techniques known to the art in order to yield tunable mechanical and biological properties (See, Qi et al., *Scientific Reports* 4: 4706 (2013)).

Additional examples of the invention include membranes as described in the previous examples, containing hydrogels, polymers, and compounds of materials which have been modified via addition of enhancing agents or compounds in order to yield tunable mechanical and biological properties. Examples of techniques include but are not limited to the addition of glycerin, sorbitol, propylene glycol, or other plasticizers into gelatin or gelatin composite hydrogels (See, F. M. Vanina et al., *Food Hydrocolloids* 19, 899-907 (2005)).

Additional examples of the invention include membranes as described in the previous examples, with the addition of a second polymer or hydrogel material providing a support matrix for the basement membrane material. This second hydrogel or polymer may be constructed of similar material as the basement membrane or may be constructed of a complimentary hydrogel or polymer.

Additional examples of the invention include membranes as described in the previous examples, where the film is partially or fully constructed of gelatin or other hydrogel material that has been altered to be photo-curable using ultraviolet light of various wavelengths, such as gelatin methacrylate. Materials such as this, in varying concentrations can be created using published protocols or techniques know to the art.

Additional examples of the invention include membranes as described in the previous examples where the membrane is fabricated in a multi-step process in order to create a membrane of mixed composition or architecture.

Additional examples of the invention include membranes as described in the previous examples where application of a curing solution or compound that acts to polymerize, gel, cure, or otherwise solidify the polymer or hydrogel material is introduced before, during, or after the membrane is formed. For example the membrane is fabricated and subsequently subjected to a crosslinking solution that may contain glutaraldehyde, transglutaminase, or other crosslinking enzymes or molecules, at but not limited to concentrations of 0.01-5 g per 10 g gelatin. Alternatively the crosslinking agent may be incorporated into the solution prior to the formation of the membrane.

Additional examples of the invention include membranes as described in the previous examples, containing hydrogels and polymers with the encapsulation or addition of biological factors to promote cell and tissue growth.

Example 2

Implantable IABBP Device

Figure 4:
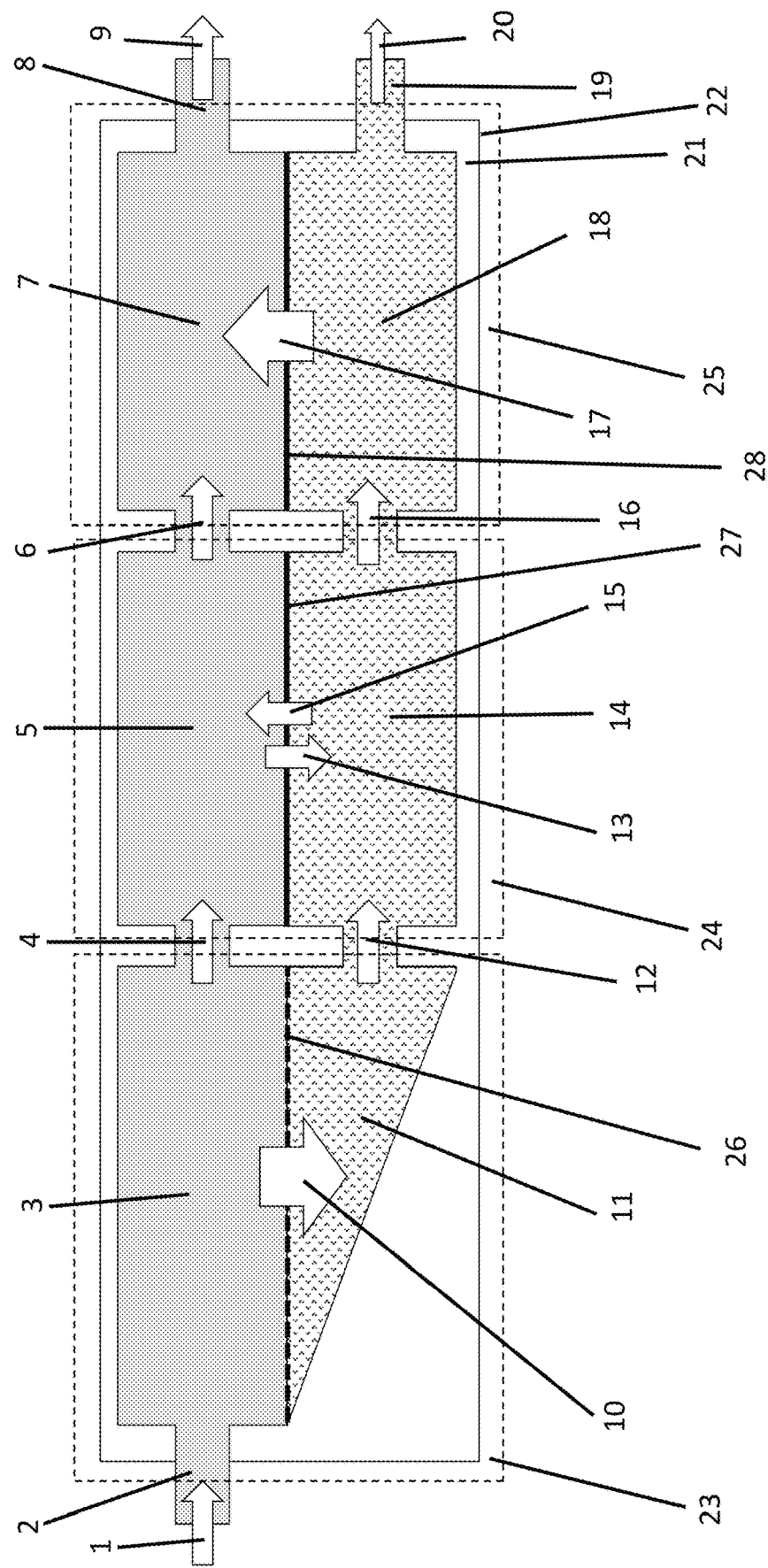
FIG. 4 shows a schematic of a single functional unit of the IABBP device. Blood flows from the recipient's artery into the filtration segment, where a primary filtrate is generated. Blood and filtrate then flow to the tubular segment in their respective channels. Absorption and Secretion occur in the tubular segment. Blood and secondary filtrate then flow into the ductal segment in their respective channels. The secondary filtrate is concentrated, and drained via a conduit, while blood is returned to the recipient's circulation. (1) Blood inflow; (2) Blood inflow conduit; (3) Filtration segment blood channel system; (4) Blood flow to tubular segment; (5) Tubular segment blood channel system; (6) Blood flow to ductal segment; (7) Ductal segment channel system; (8) Blood outflow conduit; (9) Blood outflow; (10) Filtration; (11) Filtration segment filtrate channel; (12) Filtrate flow to tubular segment; (13) Solute and water secretion; (14) Tubular segment filtrate channel system; (15) Solute and water absorption; (16) Filtrate flow to ductal segment; (17) Concentration (water absorption); (18) Ductal segment filtrate channel system; (19) Filtrate outflow conduit; (20) Filtrate outflow; (21) Embedding Matrix; (22) Capsule; (23) Filtration segment; (24) Tubular segment; (25) Ductal segment; (26) Filtration membrane; (27) Tubular membrane; (28) Ductal membrane.
Figure 6:
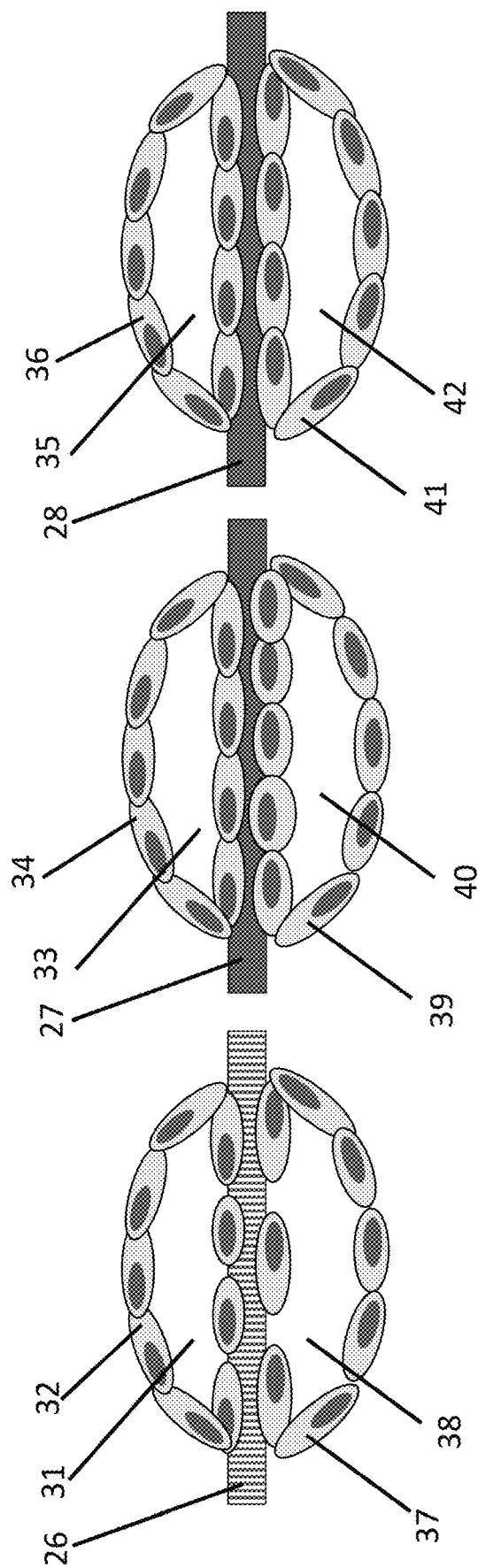
FIG. 6 shows a schematic of each segment of a functional IABBP unit repopulated with cells. Each channel system in each segment is separated by a specialized membrane and lined with specialized cells to enable higher level function. (26) Filtration segment membrane; (31) Filtration segment blood channel; (32) Filtration segment endothelial cell; (27) Tubular segment membrane; (33) Tubular segment blood channel; (34) Tubular segment endothelial cells; (28) Ductal segment membrane; (35) Ductal segment blood channel; (36) Ductal segment endothelial cells; (37) Filtration segment epithelial cell; (38) Filtration segment filtrate channel; (39) Tubular segment epithelial cell; (40) Tubular segment filtrate channel; (41) Ductal segment epithelial cell; (42) Ductal segment filtrate channel.

An implantable IABBP device for renal replacement contains one or more functional units. In each of these functional units, two separate channel systems that are separated by extracellular matrix material and lined by cells (FIG. 4 and FIG. 6). One channel system (herein referred to as vascular channel or vascular channel system) is lined with endothelial cells and perfused with blood that is gradually purified as it passes through the device. A second channel system (herein referred to as filtrate channel or filtrate channel system) is lined with epithelial cells and perfused by filtrate that is gradually processed. Blood flows into the vascular channel system from an artery and returns to a vein via vascular conduits. The filtrate is produced by the device and flows through the filtrate channel. Once fully processed, the filtrate is drained via a conduit and a surgically created fistula to an extracorporeal collection system or via a conduit and a surgical anastomosis into the patient's bladder. Within the IABBP device, the channel networks are comprised of three segments that provide distinct functions. These segments are arranged in series based on the blood through the device, so that the blood is processed sequentially by each segment before returning to the cardiovascular system.

In the first segment (herein referred to as the filtration segment), the IABBP device generates a primary ultrafiltrate via cell enhanced ultrafiltration. A fraction of the blood (the filtration fraction) is filtered from the vascular channel to the filtrate channel Blood cells, and larger molecules are retained in the vascular channel via cell and matrix mediated sieving, while water, glucose, uremic toxins such as Blood urea nitrogen (BUN) and other solutes are freely filtered.

Figure 5:
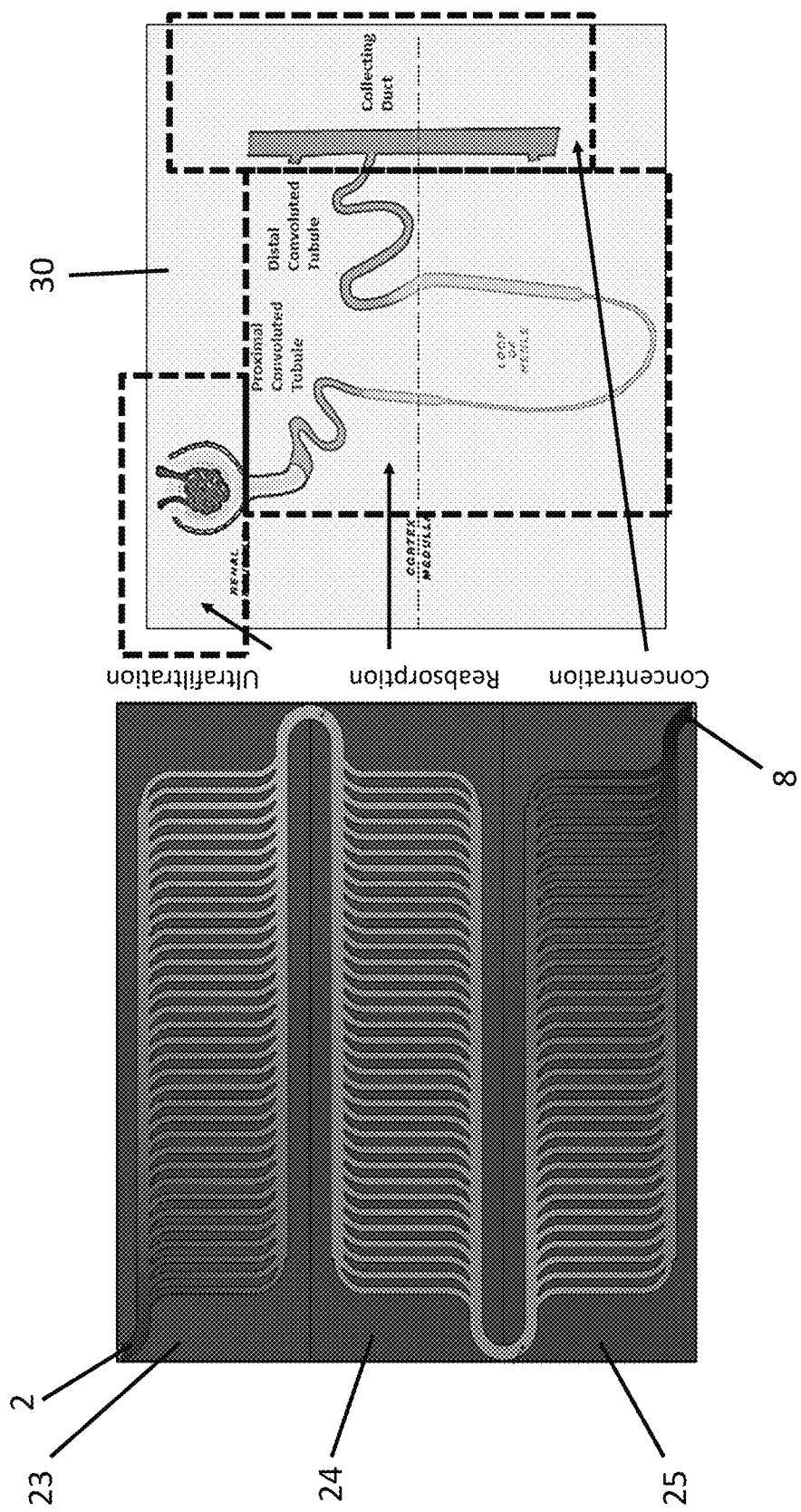
FIG. 5 shows a schematic of the channel architecture of a single functional IABBP unit. Corresponding segments of the nephron are shown to explain sequential function of each segment. (2) Blood inflow conduit; (8) Blood outflow conduit: (23) Filtration segment; (24) Tubular segment; (25) Ductal segment; (30) Corresponding segments of the human nephron.

Blood flow through the filtration segment is defined as $Q_{bf}$ and depends on arterial inflow $Q_A$ and Filtration fraction $FF_f$ ($Q_{bf}=Q_A-(Q_A*FF_f)$). Filtrate flow from the filtration segment is defined as primary filtrate flow ($Q_{ft}$) which depends on blood flow $Q_{bf}$ and filtration fraction $FF_f$ ($Q_{ft}=Q_{bf}*FF_f$) Blood pressure in the filtration segment is defined as $P_{bf}$ is a dynamic parameter determined by blood flow $Q_{bf}$, channel architecture, incoming blood pressure $P_{bA}$, and backpressure from the downstream vascular network $P_{bt}$. (FIG. 5)

Similar to blood pressure, filtrate pressure in the filtration segment is a dynamic parameter determined by channel architecture, filtrate flow, and backpressure from the downstream filtrate channel system. (FIG. 5)

In the second segment (herein referred to as the tubular segment), this primary ultrafiltrate then undergoes further modification via cell enhanced solute secretion (active and passive transport into filtrate via cells and extracellular matrix material), and absorption (active and passive removal from filtrate via cells and extracellular matrix materials) to generate a secondary filtrate. In this segment cells also contribute to active metabolic control via bicarbonate synthesis.

Blood flow through the tubular segment is defined as $Qb_t$, which equals incoming blood flow from the filtration segment $Q_{bf}$ minus the relative filtration fraction of the tubular segment ($Q_{bt}=Q_{bf}-(FF_t*Q_{bf})$). Filtrate flow from the tubular segment is defined as secondary filtrate flow $Q_{fII}$, which depends on primary filtrate flow, tubular filtration fraction $FF_t$, and tubular blood flow $Q_{bt}$ ($Q_{fII}=Q_{ft}+(Q_{bt}*FF_t)$). Blood pressure in the tubular segment is a dynamic parameter determined by incoming blood flow $Q_{bf}$, channel architecture, incoming blood pressure from the filtration segment $P_{bf}$, and backpressure from the downstream vascular network $P_{bd}$. (FIG. 5)

Similar to blood pressure, filtrate pressure in the tubular segment is defined as $P_{ft}$ and is a dynamic parameter determined by incoming filtrate flow $Q_{ft}$, channel architecture, and backpressure from the downstream filtrate channel system $P_{fd}$. (FIG. 5)

In a third segment (herein referred to as the ductal segment or ductal segment system), this secondary filtrate is then concentrated (water removal from the filtrate via cells and extracellular matrix) to generate a tertiary filtrate. The tertiary filtrate is then drained from the device as described above.

Blood flow through the ductal segment is defined as $Q_{bd}$, which equals the incoming blood flow through the tubular segment $Q_{bt}$ plus the absorption fraction of the ductal segment $AF_d$ ($Q_{bd}=Q_{bt}(AF_d*Q_{fII})$). Since the ductal segment is the final segment, blood flow through the ductal segment $Q_{bd}$ equals venous blood outflow $Q_{bv}$ ($Q_{bd}=Q_{bv}$). Filtrate flow in the ductal segment is defined as tertiary filtrate flow $Q_{fIII}$, which depends on secondary filtrate flow $Q_{fII}$ and ductal absorption fraction $AF_d$ ($Q_{fII}=Q_{ft}+(Q_{bt}*FF_t)$). Blood pressure in the ductal segment is a dynamic parameter determined by incoming blood flow $Q_{bt}$, channel architecture, incoming blood pressure from the tubular segment $P_{bt}$, and venous backpressure $P_{bV}$. (FIG. 5)

Similar to blood pressure, filtrate pressure in the ductal segment is defined as $P_{fd}$ and is a dynamic parameter determined by channel architecture, filtrate inflow from the tubular segment $Q_{ft}$, and backpressure from the filtrate drainage system $P_{fb}$. (FIG. 5)

In each segment, cells line the various channels to support its respective functions. (FIG. 6)

In the filtration segment, endothelial cells (e.g., primary human glomerular endothelial cells, induced pluripotent stem cell (iPSC) derived endothelial cells, and/or human umbilical cord endothelial cells) line the vascular channel system. These endothelial cells may form a fenestrated lining to enable filtration and sieving function. The filtration channel system in the filtration segment is lined with epithelial cells (e.g., primary human podoytes, human iPSC derived podocytes), which may further enhance filtration and sieving function.

In the tubular segment, endothelial cells (e.g., primary human peritubular capillary endothelial cells, iPSC derived endothelial cells, human umbilical cord endothelial cells) line the vascular channel system. The filtration channel system in the tubular segment is lined by epithelial cells to enable absorption and secretion of solutes and water (e.g., primary human tubular epithelial cells, and/or iPSC derived tubular epithelial cells).

In the ductal segment, endothelial cells (e.g., primary human renal medullary endothelial cells, iPSC derived endothelial cells, and/or human umbilical cord endothelial cells) line the vascular channel system. The filtration channel system in the ductal segment is lined by epithelial cells to enable reabsorption of water and concentration of the secondary filtrate to form a tertiary filtrate (e.g., primary human tubular epithelial cells, and/or iPSC derived tubular epithelial cells).

Figure 7:
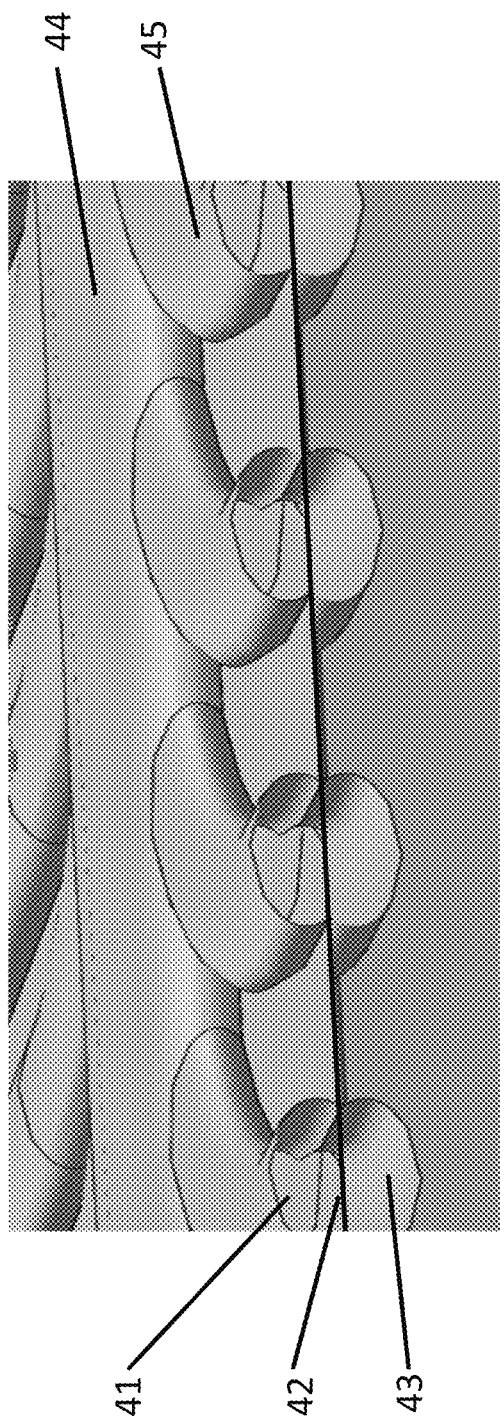
FIG. 7 shows a three-dimensional rendering of a cross-section of a functional IABBP unit. The vascular space is separated from the filtrate space by a specialized membrane.

In each segment, vascular channels and filtrate channels are separated by a membrane that supports the respective segmental function. (FIGS. 4 and 7) In the filtration segment, this membrane enables formation of a filtrate from vascular space to filtration space. In the tubular segment, this membrane enables solute and water exchange between the vascular and the filtration channel system. In the ductal segment, this membrane enables transfer of water and solutes from the filtration channel system to the vascular channel system. The membrane separating the respective channel systems can be in the form of a collagen membrane with a thickness of 0.1-10 (e.g., 0.3-10) micrometers that supports cell adhesion on both sides and is resistant to membrane fouling. The membrane may be porous to facilitate a higher filtration or reabsorption rate or increased solute exchange. The membrane may be crosslinked to various degrees to change its physical and biological properties.

The respective channel system architecture in each segment is tuned to provide a specific resistance and therefore control the hydrostatic pressure in vascular and filtrate channels to enable its respective function. The architecture of the channel system is designed to minimize turbulent flow to reduce the risk of clot formation, cell activation, or obstruction. The channel system may contain one or more branching networks and subnetworks to increase its surface area. Channels may have varying diameters to provide an even pressure across the respective segments and their membranes.

In order to increase the functional capacity to meet various patient demands, the functional units of a purification device can be stacked to function in parallel. (FIG. 8)

Table 1 describes an example of target functional specifications for a clinically usable IABBP device.

TABLE 1

Target Functional Specifications: IABBP

| | |
|---|---|
| Minimum Shear Stress | 5 dyne/cm^2 |
| Minimum Transmembrane Pressure | 10 mmHg |
| Approximate Blood Inflow Rate | 1000 mL/min |
| Minimum Blood Ultrafiltrate Rate | 27.7 mL/min |
| Minimum Ultrafiltration Fraction | 3% |
| Urine Production Rate | 1 mL/min |
| Minimum Reabsorption Fraction | 96% |

Extracorporeal IABBP Device

In one example, the IABBP is not implanted, but maintained in a sterile, heated enclosure (a bioreactor) and connected to the patient's blood circulation via cannulation of an arteriovenous fistula or a central vein. Blood can be delivered to the device with or without the aid of a mechanical pump.

Example 3—Membrane Manufacturing

In one example, in order to generate membranes for hemofiltration, a matrix solution of gelatin is prepared at a concentration of 5-30% wt. This solution can be prepared by dissolving the gelatin in water, with PBS, cell culture media, growth factors, or other enhancements. This solution is heated to 45° C. to maintain the gelatin in a sol state.

In order to generate a porous membrane, a specific volume of porogen solution containing self-assembling triblock copolymers at 1-40% wt (Pluronic F127) is added to the gelatin matrix solution. This combined matrix-porogen solution is then mixed via sonication such that the F127 is dispersed in the gelatin solution to a final concentration above the critical micelle concentration CMC and critical micelle temperature CMT, causing the F127 to form micelles and micelle aggregates which can serve as a sacrificial porogen. This combined matrix-porogen solution is then subsequently deposited onto a substrate through spin coating or other thin film deposition techniques, and depending on technique and parameters film thickness may range anywhere from 0.1-10 μm. The exact concentration of F127 in the final membrane is used to control the pore size and bulk porosity of the membrane which directly correlates with the diffusion and filtration capacity of the acellular membrane. This, in turn, will dictate the functional capacity of the membrane when it is cellularized. For example, in order to produce a membrane that provides a functional filtration rate (0.2-2 ml per minute) in the context of the first segment (filtration segment) of the IABBP, a membrane is fabricated using 25 ml of 30% wt gelatin mixed with 3.15 ml of 35% wt F127 stock solution, which provides us with roughly a 4.00% wt F127 concentration in the working solution. This solution is then throughout mixed and degassed and deposited onto a substrate during spin coating and allowed to dry before removal and subsequent crosslinking. This membrane provides a range of filtration rates suitable for filtration function within the context of the IABBP (FIG. 12), and the exact rate and overall porosity can be increased or decreased to achieve desired function. Pore size and distribution can be analyzed using experimental methods such as fluorescent bead analysis using the membrane testing system as described below, or in a more quantitative manner using image analysis of the pores which can provide distribution and other data not available through experimental methods (FIG. 13).

The thin film is then allowed to dry and is removed from the substrate. At this point, the film is dry and non-crosslinked, and may be incorporated into a scaffold or other such biologic structure and crosslinked. This can be done by mounting the film into a frame which allows for 3D printing or other deposition of sacrificial material on either side of the membrane to create opposed channel networks. This film and channel construct can subsequently be embedded into a scaffold and crosslinked. Once crosslinked the sacrificial material can be removed, and the channels can be perfused. It is possible to dissolve and remove the Pluronic F127 micelles in the membrane using isopropanol or other nonpolar solvents that disrupt the micelle core, which can be perfused through the scaffold to open the pores in the membrane. Alternatively, this dried film may be crosslinked by soaking in glutaraldehyde solution or other crosslinking agent (such as transglutaminase). The sacrificial porogen material can then be removed by additional soaking of the film in solvent. Once the porogen material has been removed, the film can be rinsed with PBS or other solution to remove any remaining crosslinking agent or solvent, and subsequently populated with cells as needed.

Cellularized or acellular membranes may be tested in an in-vitro isolated membrane apparatus (FIGS. 12A-12B). Briefly, the isolated membrane is placed between two support pieces or mesh screens of high porosity and low resistance to allow for uninhibited filtration or flow, and designed to expose the substantial entirety of the membrane surface area. These support pieces or meshed screens are clamped in place between two halves of a chamber containing ports that allow for perfusion with fluid or gas or a combination of both in order to simulate in-vivo membrane function. This type of chamber and testing system allows for short term or extended testing of cellularized or acellular membranes in a high throughput manner Data produced by this system can be correlated with known membrane surface area to provide functional data normalized to surface area, which can inform device design.

Example 4—Manufacturing of Various Channel Patterns on Thin Film Membrane

Channel architectures can be precisely controlled using extrusion-based 3D printing technology to print channels out of sacrificial materials on either side of the membrane. The entire device is then embedded into an extracellular matrix material (e.g., scaffold) and the sacrificial material is evacuated, resulting in two channel networks, one on either side of the membrane. The architecture and dimensions of the channels composing these networks is designed using computer aided design (CAD) software, then converted into G-code to control the 3D printing process. Channel diameter can be modulated by varying the 3D printer motor speed, the amount of pressure driving extrusion, and the temperature of the extruder head, all of which are controlled through G-code and the associated 3D printer electronics. For example, in order to create a tapered channel which increases in diameter, the motor speed moving the extruder print head can be controlled to move increasingly slower along the length of the channel while keeping all other parameters constant. Alternatively, the pressure driving extrusion can be increased along the length of the channel while keeping all other parameters constant to increase the rate of printed material extrusion. The interplay of these varying parameters can be calibrated and used to print the desired channel geometries. Precise control of channel geometry and architecture enables control of the hydrostatic pressure and flow patterns throughout the channel networks and across the thin membrane.

Example 5—Manufacturing of a Multilayered Device

Multiple layers of channel networks can be stacked to increase the functional surface area of an IABBP device (FIG. 9). The supporting scaffold of the device is assembled by first pouring 20 mL of 20% gelatin, 10% transglutaminase (20 U/mL) into a bottom mold (i.e., extracellular matrix material). Prepared inflow and outflow conduits are then filled with Pluronic F127 and placed in the recessed grooves of the bottom mold (FIG. 10). The conduits are half submerged in the gelatin. The gelatin in the mold is allowed to thermally and enzymatically crosslink. Gelatin can crosslink at cooler temperatures, but this crosslinking can be reversed by warming the gelatin. Crosslinking with an enzyme such as transglutaminase or with glutaraldehyde is permanent. A thin film membrane is sandwiched between two frames. The framed membrane is printed on one side with Pluronic F127 in the desired pattern using air from a pressure-controlled extrusion assembly. When dry, the framed membrane is lifted, flipped, and printed on the opposite side with Pluronic F127 in a mirrored pattern that produces channel networks opposed across the membrane. The printed membrane is then air dried. When the printed membrane is dry, another 10 mL of 20% gelatin, 10% transglutaminase is poured into the mold. This gelatin layer should cover the conduits completely. The membrane is placed onto the gelatin without the inclusion of air, for instance by mechanical means, and the channel networks are aligned with the conduits to produce continuous networks. The membrane bonds to the gelatin as it is lowered into place. After the gelatin sets, excess membrane is cut from the frame, and the frame is removed. Another membrane is framed and printed, and when dry, a spacer is placed on top of the first layer. At this point shafts or pillars of F127 may be added to the channel pattern on lower membrane that will align with and connect to the upper membrane channel networks, thereby creating a continuous multilayer network. If necessary, holes can be punched, dissolved, or otherwise removed from the membranes to allow for interlayer connections. This next spacer is filled with 10 mL of 20% gelatin, 10% transglutaminase, and the next membrane is lowered into place. The membrane is lowered onto the next layer such that the networks on each layer are aligned. This process can be repeated for as many layers as required. During assembly as previously described, or after the final membrane is placed, each layer may be connected via small shafts that may be filled with Pluronic F127 or other fluid or gel that can be evacuated. These connections are created along the height of the graft in order to connect the channel networks of the various layers. Care is taken to connect like to like (e.g., vascular to vascular and filtrate to filtrate). A prepared conduit filled with Pluronic F127 is placed on the top membrane in order to make contact with the vascular channel system or filtration channel system and provide a location for anastomosis of the graft to vasculature or for cannulation. A taller spacer with a notch for the conduit is then placed onto of the top membrane, and the mold is filled with 20 mL of 20% gelatin and 10% transglutaminase to seal in the channel networks and complete the multilayered graft. Alternatively, the interior connection between membrane layers may occur once the scaffold is fully assembled by using a punch or other instrument to remove gelatin and create a hollow shaft or other connection between layers. This space may be filled with Pluronic F127 and then may be plugged, filled, or otherwise sealed with gelatin or other material that may be bonded, crosslinked, glued, or otherwise adhered in place to close any remaining hole and maintained the integrity of the channel networks.

Example 6—Primary Cell Isolation from Discarded Kidneys

Primary cells are isolated from human kidneys deemed unsuitable for transplantation. Renal cortex is manually separated from the medulla and minced into pieces smaller than 2 mm in diameter. Minced tissue is digested in collagenase type IV solution at a concentration of 200 U/ml for one hour at 37 degrees under constant agitation (150 RPM). After digestion, collagenase in tissue slurry is neutralized by addition of fetal bovine serum at a final concentration of 10% and digest filtered in series through sifters with 250 μm and 125 μm pore sizes. Glomeruli are collected from the top of the 125 μm sifter and tubules from the flow-through. Both portions are allowed to attach on gelatin coated plastic. Media formulation is designed to promote epithelial and endothelial cell maintenance and specified in table # (co-culture media). After one week in culture, cells are harvested by EDTA treatment to obtain a single cell suspension and further separated into specific cell types. From the glomerular portion, glomerular endothelial cells and podocytes are obtained by immune-separation with CD31 and Nephrin antibodies respectively. Contaminating fibroblasts are depleted by Thy1 immuno-separation. From the flow-through, peritubular endothelial cells are separated from cortical epithelial cells (proximal and distal tubule) by CD31 and CK18 immuno-separation respectively. Contaminating fibroblasts are also depleted from these portions by Thy1 immuno-separation. Medullar tissue is processed in a similar manner and collecting duct cells isolated by L1CAM immune-separation with fibroblast depletion with Thy1 immuno-separation. Media formulations for specific cell types described in Tables 2-4).

TABLE 2

Endothelial Media

| | |
|---|---|
| FBS | 5% |
| EGF | 5 ng/ml |
| VEGF | 5 ng/ml |
| FGF2 | 5 ng/ml |
| IGF1 | 15 ng/ml |
| L-Alanyl-L-Glutamine | 1.0 mM |
| Hydrocortisone | 1 µg/ml |
| Heparin | 0.75 U/ml |
| Ascorbic Acid | 50 µg/ml |

TABLE 3

Epithelial Media

| | |
|---|---|
| FBS | 0.50% |
| EGF | 1.0 ng/ml |
| Insulin | 5 µg/ml |
| Epinepherine | 1 µM |
| Transferrin | 5 µg/ml |
| L-Alanyl-L-Glutamine | 2.5 mM |
| Hydrocortisone | 100 ng/ml |
| Triiodothyronine | 10 nM |

TABLE 4

Co-culture Media

| | |
|---|---|
| FBS | 5% |
| EGF | 10 ng/ml |
| VEGF | 5 ng/ml |
| FGF2 | 5 ng/ml |
| IGF1 | 15 ng/ml |
| L-Alanyl-L-Glutamine | 10 mM |
| Hydrocortisone | 1 µg/ml |
| Heparin | 0.75 U/ml |
| Ascorbic Acid | 50 µg/ml |
| Insulin | 5 µg/ml |
| Epinepherine | 1 µM |
| Transferrin | 5 µg/ml |
| Triiodothyronine | 10 nM |

Example 7—Cell Seeding onto an IABBP Scaffold

Vascular channels and filtration channels are respectively lined with confluent monolayers of endothelial or epithelial cells in order to provide their respective functions. To seed cells into the channels, the inlet and outlet conduits to both networks are cannulated and a suspension of the appropriate cell type is injected into the inlet conduit for either the vascular or filtration channels. Fluid is simultaneously pulled from each outlet conduit at the same rate as the cell suspension is injected until the entire network is filled with cell suspension. Cells are allowed to attach to the channel walls under static culture in an incubator at 37° C. for at least 1 hour then the entire device is rotated 180° and seeded again with the same respective cell suspensions in both the vascular and filtration networks to ensure seeding of the full channel lumens. After this time, networks are perfused with media and left for at least 24 hours to achieve full confluence. Direct flow of cell media, blood, or serum may be introduced into each channel network to supply nutrients and oxygen to cells and to enhance cellular function of both endothelial and epithelial cells. Flow can be controlled using either pumps or gravity-driven flow.

In order to seed multiple cell types into a single channel network, it is necessary to seed each type sequentially based on the location in the scaffold. It is important to note that the scaffold channel networks can be perfused in either direction, which enables this type of sequential seeding. In order to seed podocytes and other glomerular epithelial cell types into segment 1, followed by tubule cells into segment 2, and distal and collecting duct cells into segment 3, it is necessary to suspend each cell type or mixture of cell types into a volume proportional to the volume of the segment which they are to occupy.

Once the cells are in a dense suspension, the cells intended for segment 1 may be infused through the cannula adjacent to segment 1 such that the entirety of segment 1 is filled with cell suspension and segment 2 is filled with the acellular fluid that was previously located in segment 1. These cells are allowed to adhere for 30 minutes up to 3 hours or more, and a volume of fluid equal to the suspension volume is infused through the cannula adjacent to segment 3 in order to flush out the remaining cell suspension media and any cells that did not attach in segment 1. The scaffold is then flipped and the procedure repeated to provide full coverage of segment 1 with the desired cell types.

Then a volume of the second cell suspension containing cells for segment 2 that is equal to the volume of the segment 2 channels in infused into the scaffold through the cannula adjacent to segment 1. Then a volume of solution equal to the volume of the segment 1 channels containing no cells is infused into the cannula adjacent to segment 1 such that the cell suspension for segment 2 is pushed through the channels to fill segment 2 but does not enter segment 3. The cells are allowed to adhere for 30 minutes up to 3 hours. Then a solution without cells of a volume equal or greater than the combined volumes of segment 1 and segment 2 is infused through the cannula adjacent to segment 3 in order to flush out remaining cell suspension media and cells that did not adhere. The scaffold is then flipped and the procedure repeated to provide full coverage of segment 2 with the desired cell types.

Then a volume of the third cell suspension containing cells for segment 3 that is equal to the volume of the segment 3 channels in infused into the scaffold through the cannula adjacent to segment 1. Then a volume of solution equal to the combined volume of the segment 1 channels and segment 2 channels containing no cells is infused into the cannula adjacent to segment 1 such that the cell suspension for segment 3 is pushed through the channels to fill segment 3. The cells are allowed to adhere for 30 minutes up to 3 hours. Then a solution without cells of a volume equal or greater than the combined volumes of segment 1, segment 2, and segment 3 is infused through the cannula adjacent to segment 3 in order to flush out remaining cell suspension media and cells that did not adhere. The scaffold is then flipped and the procedure repeated to provide full coverage of segment 3 with the desired cell types.

At this point the scaffold channel network is fully lined with the desired cell types which have been located in the desired segment so as to produce coordinated function across the entire device. This process is repeatable and can be expanded should additional segments be included. The order of filling segments with cells may also be rearranged, depending on need. Further, the order of scaffold flipping may also be changed, depending on need. For example, cells in each segment may all be adhered to the membrane or matrix (e.g., gelatin matrix) in a step wise fashion followed by a single flipping of the membrane to adhere cells to each of the other segments. This type of sequential cell seeding could be accomplished in other ways using the know volume of the channels, and does not necessarily have to happen in the order or manner described here, cells could be added in a sequential order via one way perfusion without reverse perfusion to back-flush cell suspension and cells that did not adhere.

Example 8—In Silico Modeling of an IABBP Device and its Function and In Vitro Model of IABBP Membrane A virtual model is generated using SolidWorks (SW). A 3D point cloud is brought from the 3D printer into Geomagic and then into SW. The model in SolidWorks allows the device to be simulated under various clinical conditions to better understand its performance. For instance, when 65 mmHg is applied to the inflow conduit, we can calculate the ultrafiltration rate of the device on the efferent side. A membrane is interpositioned in the device and it is given the performance characteristics instructed by an in vitro membrane testing apparatus, that allows for benchtop testing of various acellular and cellular membranes (FIGS. 12A-12B). These key characteristics drive and validate the output numbers we get from the model. This allows us to tune the 2 key parameters of the device: surface area and number of repeated layers we will have in parallel filtering blood.

Example 9—Fiber Membrane Manufacture

In step 1, a solution of gelatin, collagen, fibrin, or other biologic or synthetic matrix material is created. In step 2, dried silk nano and micro-scale fibers are added to the matrix solution and mixed by stirring. Size of fibers depends on preparation and the size composition of the fiber component can be tuned to yield desirable mechanical properties. This fiber component may be crosslinked to itself or bonded to the matrix component in subsequent steps to yield interpenetrating networks of matrix and fiber. In step 3, a solution containing a sacrificial porogen material is combined with the matrix and fiber solution created in step 1 and thoroughly mixed. In step 4, the matrix-porogen solution is deposited onto a substrate through spin coating, dip coating, or other such thin film deposition techniques and allowed to dry, gel, or otherwise solidify. This deposition technique allows for fine control over film thickness. In step 5, additional layers of similar or dissimilar composition are optionally deposited onto the first layer to create a composite or layered film. Alternatively, additional layers are deposited in a manner allowing for patterning or other spatial organization within the membrane. In step 6, the sacrificial porogen material is removed through dissolution, degradation, or other destructive techniques leaving an empty space in the thin film that serves as a pore.

What is claimed is:

1. An apparatus for integrated adaptive biologic blood purification comprising:
   a functional unit comprising
      a membrane comprising a vascular surface and a filtration surface;
      a vascular channel system comprising a first luminal space, adhered to and in fluid communication with the vascular surface of the membrane, and comprising a first end configured to connect in fluid communication to a fluid supply and a second end configured to connect in fluid communication to a filtered fluid outlet;
      a filtration channel system comprising a second luminal space, adhered to and in fluid communication with the filtration surface of the membrane, and comprising a third end configured to connect in fluid communication to a filtrate outlet;
      wherein the vascular channel system and the filtration channel system are in fluid communication with each other across the membrane;
      wherein the functional unit further comprises at least three segments, including at least a filtration segment configured to provide ultrafiltration producing a primary ultrafiltrate, connecting to a tubular segment configured to provide reabsorption producing a secondary ultrafiltrate, connecting to a ductal segment configured to provide concentration producing a tertiary ultrafiltrate; and
      wherein the membrane comprises three membrane segments including at least a filtration membrane segment, a tubular membrane segment and a ductal membrane segment.

2. The apparatus of claim 1, wherein the membrane comprises a biocompatible extracellular matrix membrane separating the vascular channel system from the filtration channel system, the biocompatible extracellular matrix membrane is embedded into a matrix material.

3. The apparatus of claim 2, wherein the biocompatible extracellular matrix membrane comprises a collagen membrane with a thickness of 0.1-10 micrometers (0.1-10 µm) that supports cell adhesion on both the vascular surface and the filtration surface of the collagen membrane.

4. The apparatus of claim 1, wherein the membrane is configured to have a minimum shear stress of 5 dyne/cm$^2$ and/or a minimum transmembrane pressure of 10 mmHg.

5. The apparatus of claim 1, wherein
   the filtration membrane segment enables production of a filtrate from the first luminal space in the vascular channel system to the second luminal space of the filtration channel system;
   the tubular membrane segment enables solute and water exchange and/or diffusion between the vascular channel system and the filtration channel system; and
   the ductal membrane segment enables transfer of water and solutes from the filtration channel system to the vascular channel system.

6. The apparatus of claim 1, wherein the functional unit comprises at least one biological fluid inflow conduit in fluid communication with the first end of the vascular channel system and the first luminal space and at least one biological fluid outflow conduit in fluid communication with the second end of the vascular channel system and the first luminal space, wherein the functional unit comprises at least one filtrate outflow conduit in fluid communication with the third end of the filtration channel system and the second luminal space, and wherein the functional unit further comprises one or more vascular segment conduits interconnecting the filtration segment, the tubular segment and the ductal segment of the vascular channel system and the first luminal space and one or more filtration segment conduits interconnecting the filtration segment, the tubular segment and the ductal segment of the filtration channel system and the second luminal space.

7. The apparatus of claim 6, wherein the at least one biological fluid inflow conduit is in fluid communication with an arterial conduit, the at least one biological fluid outflow conduit is in fluid communication with a vascular conduit, and the at least one filtrate outflow conduit is in fluid communication with a drain conduit.

8. The apparatus of claim 7, wherein the apparatus produces an ultrafiltrate that is drained, using a drain conduit, into an extracorporeal collection system or drained, using a drain conduit, into a patient bladder.

9. The apparatus of claim 1, wherein the first luminal space and the second luminal spaces are embedded in a scaffold.

10. The apparatus of claim 1, wherein:
the filtration segment of the vascular channel system comprises vascular channel walls lined with endothelial cells selected from primary human glomerular endothelial cells, induced pluripotent stem cell (iPSC) derived endothelial cells, and/or human umbilical cord endothelial cells;
the tubular segment of the vascular channel system comprises vascular channel walls lined with endothelial cells selected from primary human peritubular capillary endothelial cells, iPSC derived endothelial cells, and/or human umbilical cord endothelial cells; and
the ductal segment of the vascular channel system comprises vascular channel walls lined with endothelial cells selected from primary human renal medullary endothelial cells, iPSC derived endothelial cells, and/or human umbilical cord endothelial cells.

11. The apparatus of claim 1, wherein:
the filtration segment of the filtration channel system comprises filtration channel walls lined with epithelial cells selected from primary human podocytes and/or human iPSC derived podocytes;
the tubular segment of the filtration channel system comprises filtration channel walls lined with epithelial cells selected from primary human tubular epithelial cells and/or iPSC derived tubular epithelial cells; and
the ductal segment of the filtration channel system comprises filtration channel walls lined with epithelial cells selected from primary human tubular epithelial cells and/or iPSC derived tubular epithelial cells.

12. The apparatus of claim 1, wherein the endothelial and/or epithelial cells are allogenic or autologous to a patient using the apparatus.

13. The apparatus of claim 1, wherein the apparatus comprises a plurality of functional units, including the functional unit and additional functional units of a same configuration, wherein each functional unit of the plurality of functional units has:
a first end of a vascular channel system and first luminal space in fluid communication with the at least one biological fluid inflow conduit;
a second end of a vascular channel system and first luminal space in fluid communication with the at least one biological fluid outflow conduit, and
a third end of a filtration channel system and second luminal space in fluid communication with a filtrate outflow conduit;
wherein each first end of the plurality of functional units connects individually and in parallel to one of a plurality of manifold ports of the at least one biological fluid inflow conduit; wherein each second end of the plurality of functional units connects individually and in parallel to one of a plurality of manifold ports of the at least one biological fluid outflow conduit; and wherein each third end of the plurality of functional units connects individually and in parallel to one of a plurality of manifold ports of the at least one filtrate outflow conduit.

14. The apparatus of claim 13, wherein the apparatus comprises the plurality of functional units, including the functional unit and the additional functional units of a same configuration, stacked in parallel layers of functional units.

15. The apparatus of claim 1, wherein the at least one biological fluid inflow conduit comprises a blood inlet conduit configured to transport a Blood inflow, the at least one biological fluid outflow conduit comprises a blood outflow conduit configured to transport a blood outflow, and parallel layers of functional units configured for biologic blood purification.

16. The apparatus of claim 15, wherein the filtration segment of the filtration channel system is configured to provide ultrafiltration producing a primary ultrafiltrate, the tubular segment is configured to provide reabsorption producing a secondary ultrafiltrate flow by solute and water absorption, and the ductal segment is configured to provide concentration producing a tertiary ultrafiltrate flow by water absorption.

17. The apparatus of claim 1, wherein the apparatus is configured for extracorporeal operation in a sterile, heated enclosure.

18. The apparatus of claim 17, wherein blood or dialysis fluid from the peritoneal cavity is delivered to the apparatus with a mechanical pump.

19. The apparatus of claim 1, wherein the apparatus is disposed within a capsule, and sized and configured for placement within a human body to replace or augment a kidney or liver function.

20. The apparatus of claim 1, wherein the membrane comprises a porous membrane that comprises pores disposed to interconnect the vascular surface and the filtration surface, and wherein the pores have a diameter of between 1 μm and 15 μm.

* * * * *